US008586340B2

(12) United States Patent
Tsao et al.

(10) Patent No.: US 8,586,340 B2
(45) Date of Patent: Nov. 19, 2013

(54) SELECTIVE POSTTRANSLATIONAL MODIFICATION OF PHAGE-DISPLAYED POLYPEPTIDES

(75) Inventors: Meng-Lin Tsao, San Diego, CA (US); Feng Tian, San Diego, CA (US); Peter Schultz, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 1062 days.

(21) Appl. No.: 11/580,223

(22) Filed: Oct. 11, 2006

(65) Prior Publication Data

US 2007/0178448 A1  Aug. 2, 2007

Related U.S. Application Data

(60) Provisional application No. 60/726,137, filed on Oct. 12, 2005, provisional application No. 60/737,622, filed on Nov. 16, 2005.

(51) Int. Cl.
*C12N 7/02* (2006.01)
*C40B 40/02* (2006.01)

(52) U.S. Cl.
USPC ............ 435/239; 435/235.1; 435/5; 530/350

(58) Field of Classification Search
USPC .......................................... 435/239, 235.1, 5
See application file for complete search history.

(56) References Cited

U.S. PATENT DOCUMENTS

| | | | |
|---|---|---|---|
| 6,107,059 A * | 8/2000 | Hart | 435/69.7 |
| 6,927,042 B2 | 8/2005 | Schultz et al. | |
| 7,045,337 B2 | 5/2006 | Schultz et al. | |
| 7,083,970 B2 | 8/2006 | Schultz et al. | |
| 7,183,082 B2 | 2/2007 | Schultz et al. | |
| 7,199,222 B2 | 4/2007 | Schultz et al. | |
| 7,217,809 B2 | 5/2007 | Schultz et al. | |
| 7,238,510 B2 | 7/2007 | Schultz et al. | |
| 7,262,040 B2 | 8/2007 | Schultz et al. | |
| 2004/0198637 A1 | 10/2004 | Schultz et al. | |
| 2004/0265952 A1 | 12/2004 | Deiters et al. | |
| 2005/0009049 A1 | 1/2005 | Chin et al. | |
| 2005/0136513 A1 | 6/2005 | Zhang et al. | |
| 2005/0208536 A1 | 9/2005 | Schultz et al. | |
| 2005/0227318 A1 | 10/2005 | Alfonta et al. | |
| 2005/0272121 A1 | 12/2005 | Xie et al. | |
| 2006/0063244 A1 | 3/2006 | Schultz et al. | |
| 2006/0068478 A1 | 3/2006 | Schultz et al. | |
| 2006/0073507 A1 | 4/2006 | Deiters et al. | |
| 2006/0110784 A1 | 5/2006 | Deiters et al. | |
| 2006/0110796 A1 | 5/2006 | Schultz et al. | |
| 2006/0134746 A1 | 6/2006 | Deiters et al. | |
| 2006/0160175 A1 | 7/2006 | Anderson et al. | |
| 2006/0177900 A1 | 8/2006 | Anderson et al. | |
| 2006/0216760 A1 * | 9/2006 | Dieterich et al. | 435/7.5 |
| 2006/0234367 A1 | 10/2006 | Schultz et al. | |
| 2006/0246509 A1 | 11/2006 | Deiters et al. | |
| 2007/0009990 A1 | 1/2007 | Alfonta et al. | |
| 2007/0020634 A1 | 1/2007 | Anderson et al. | |
| 2007/0042461 A1 | 2/2007 | Anderson et al. | |
| 2007/0099249 A1 * | 5/2007 | Abbott et al. | 435/7.5 |
| 2007/0111193 A1 | 5/2007 | Zhang et al. | |
| 2007/0154952 A1 | 7/2007 | Chin et al. | |
| 2007/0166791 A1 | 7/2007 | Chin et al. | |
| 2007/0172915 A1 | 7/2007 | Schultz et al. | |
| 2007/0184517 A1 | 8/2007 | Schultz et al. | |
| 2008/0132681 A1 * | 6/2008 | Hays et al. | 530/351 |

FOREIGN PATENT DOCUMENTS

| | | | |
|---|---|---|---|
| WO | WO 2002/086075 A2 | 10/2002 | |
| WO | WO 2004/035743 A2 | 4/2004 | |
| WO | WO 2004/094593 A2 | 11/2004 | |
| WO | WO 2005/003294 A2 | 1/2005 | |
| WO | WO 2005/007624 A2 | 1/2005 | |
| WO | WO 2005/007870 A2 | 1/2005 | |
| WO | WO 2005/019415 A2 | 3/2005 | |
| WO | WO 2006038184 * | 4/2006 | |
| WO | WO 2006/110182 A2 | 12/2006 | |

OTHER PUBLICATIONS

Anderson et al. (2002) "An expanded genetic code with a functional quadruplet codon," *PNAS*, 101:7566-7571.
Kiick et al. (2001) "Incorporation of azides into recombinant proteins for chemoselective modification by the Staudinger ligation," *PNAS*, 99:19-34.
Noren et al. (1989) "A general method for site-specific incorporation of unnatural amino acids into proteins," *Science*, 244:182-188.
Sandman et al. (2000) "Phage display of selenopeptides," 122:960-961.
Tian et al. (2004) "A phage display system with unnatural amino acids," *JACS*, 126:15962-15963.
Wang et al. (2001) "Expanding the genetic code of *Escherichia coli*," *Science*, 292:498-500.
Anderson et al. (2004) "An expanding genetic code with functional quadruplet codon," *PNAS*, 101(20) 7566-7571.
Bain et al.( 1989) "Biosynthetic site specific incorporation of a non-natural amino acid into a polypeptide," *J. Am. Chem. Soc.*, 111:8013-8014.
Chin and Schultz, (2002) "In vivo Photocrosslinking with Unnatural Amino Acid Mutagenesis," *ChemBioChem*, 11:1135-1137.
Chin et al. (2003) "An Expanded Eukaryotic Genetic Code." *Science*, 301:964-967.

(Continued)

*Primary Examiner* — Teresa Wessendorf
(74) *Attorney, Agent, or Firm* — Quine Intellectual Property Law Group, P.C.

(57) ABSTRACT

The invention relates to posttranslational modification of phage-displayed polypeptides. These displayed polypeptides comprise at least one unnatural amino acid, e.g., an aryl-azide amino acid such as p-azido-L-phenylalanine, or an alkynyl-amino acid such as para-propargyloxyphenylalanine, which are incorporated into the phage-displayed fusion polypeptide at a selected position by using an in vivo orthogonal translation system comprising a suitable orthogonal aminoacyl-tRNA synthetase and a suitable orthogonal tRNA species. These unnatural amino acids advantageously provide targets for posttranslational modifications such as azide-alkyne [3+2] cycloaddition reactions and Staudinger modifications.

10 Claims, 9 Drawing Sheets

(56) References Cited

OTHER PUBLICATIONS

Chin et al. (2002) "Addition of p-Azido-L-phenylalanine to the genetic code of *Escherichia coli.*" *J Am Chem Soc* 124(31):9026-9027.
Chin et al. (2002) "Addition of a photocrosslinking amino acid to the genetic code of *Escherichia coli.*" *PNAS*, 99(17):11020-11024.
Deiters & Schultz (2005) "In vivo incorporation of an alkyne into proteins in *Escherichia coli,*" *Bioorganic & Medicinal Chemistry Letters*,15:1521-1524.
Deiters et al. (2003) "Adding Amino Acids with Novel Reactivity to the Genetic Code of *Saccharomyces cerevisiae," J. Am. Chem. Soc.*, 125:11782-11783.
Ellman et al.( 1991) "Biosynthetic method for introducing unnatural amino acids site-specifically into proteins," *Methods Enzymol.*, 202:301-336.
Hirao et al. (2002) "An unnatural base pair for incorporating amino acid analogues into protein," *Nature Biotechnology*, 20:177-182.
Hohsaka and Sisido (2002) "Incorporation of non-natural amino acids into proteins." *Current Opinion in Chemical Biology*, 6: 809-815.
Huisgen. "1,3, Dipolar Cycloadditions—Introduction, Survey, Mechanism," *1,3-Dipolar Cycloaddition Chemistry*, [Padwa, A., Ed.] Wiley: New York, 1984; v.1,p. 1-176.
Lemieux and Bertozzi (1998) "Chemoselective ligation reactions with proteins, ologosaccharides and cells," *TIBTECH*, 16:506-513.
Li et al., (2002) "In vitro selection of mRNA display libraries containing an unnatural amino acid," *J. Am. Chem. Soc.*,124(34):9972-9973.
Link and Tirrell. (2003) "Cell surface labeling of *Escherichia coli* via copper(I)-catalyzed [3+2] cycloaddition," *J. Am. Chem. Soc.*, 125(37):11164-11165.
Liu et al. (2003) "A method for the generation of glycoprotein mimetics," *JACS*, 125(7):1702-1703.
Muir (2003 )"Semisynthesis of proteins by expressed protein ligation," *Annu. Rev. Biochem.*, 72:249-289.
Padwa. "Intermolecular 1,3-Dipolar Cycloadditions," *Comprehensive Organic Synthesis*, Trost, B.M.; Fleming, I. (Eds.), Pergamon Press, Oxford, 1991, vol. 4, pp. 1069-1109.

Pastrnak & Schultz (2001) "Phage selection for site specific incorporation of unnatural amino acids into proteins in vivo." *Bioorganic & Medicinal Chemistry*, 9:2373-2379.
Prescher et al. (2004) "Chemical remodeling of cell surfaces in living animals," *Nature*, 430:873-877.
Rodi & Makowski (1999) "Phage-display technology—finding a needle in a vst molecular haystack," *Current Opinion in Biotechnology*, 10:87-93.
Rostovtsev et al. (2002) "A stepwise Huisgen cycloaddition process: copper(I)-catalyzed regioselective "ligation" of azides and terminal alkynes," *Angew Chem Int Ed.41*:2596-2599.
Saxon and Bertozzi (2000) "Cell surface engineering by a modified Staudinger reaction," *Science*, 287:2007-2010.
Sidhu (2001) "Engineering M13 for phage display," *Bimolecular Engineering*, 18:57-63.
Smith and Petrenko (1997) "Phage display," Chem. Rev., 97:391-410.
Staudinger and Meyer (1919)"Ueber neue organische Phosphorverbindungen II. Phosphazine,"*Helv. Chim. Acta*, 2 (1):635-646.
Tornoe et al. (2002) "Peptidotriazoles on solid phase: [1,2,3]-triazoles by regiospecific copper(i)-catalyzed 1,3-dipolar cycloadditions of terminal alkynes to azides," *J. Org. Chem.*, 67(9):3057-3064.
Wang and Schultz (2005) "Expanding the Genetic Code," *Angewandte Chemie Int. Ed.*, 44(1):34-66.
Wang & Schultz. (2002) "Expanding the genetic code," *Chem. Commun.*, 1:1-11.
Wang and Schultz (2005) "Die erweiterung des genetischen codes," *Angew. Chem.*, 117, 34-68.
Wang et al. (2003) "Bioconjugation by copper(I)-catalyzed azide-alkyne [3+2] cycloaddition,"*J. Am. Chem. Soc.*, 125(11):3192-3193.
Wang et al. (2003) "Addition of the keto functional croup to the genetic code of *Escherichia coli.*" *PNAS*, 100(1):56-61.
Willats (2002) "Phage display: practicalities and prospects," *Plant Molecular Biology* 50:837-854.
Xie & Schultz. (2005) "An expanding genetic code," *Methods*, 36(3):227-238.
Zhang et al. (2004) "Selective incorporation of 5-hyroxytryptophan into proteins in mammalian cells," *Proc. Natl. Acad. Sci. U.S.A.*, 101(24):8882-8887.

\* cited by examiner

| SEQ ID NO: | Description | SEQUENCE |
|---|---|---|
| 1 | *Methanococcus jannaschii* - suppressor tyrosyl-tRNA$_{CUA}$ mutRNA$_{CUA}^{Tyr}$ | CCGGCGGUAGUUCAGCAGGGCAGAACGGCGGACUCUAAAUCCG CAUGGCGCUGGUUCAAAUCCGGCCCGCCGGACCA |
| 2 | Wild-type *Methanococcus jannaschii* tyrosyl-tRNA synthetase (MjTyrRS) amino acid sequence | MDEFEMIKRNTSEIISEEELREVLKKDEKSAYIGFEPSGKIHL GHYLQIKKMIDLQNAGFDIIILLADLHAYLNQKGELDEIRKIG DYNKKVFEAMGLKAKYVYGSEFQLDKDYTLNVYRLALKTTLKR ARRSMELIAREDENPKVAEVIYPIMQVNDIHYLGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 3 | Wild-type *Methanococcus jannaschii* tyrosyl-tRNA synthetase (MjTyrRS) nucleotide sequence | ATGGACGAATTTGAAATGATAAAGAGAAACACATCTGAATTATCAGC GAGGAAGAGTTAAGAGAGGTTTTAAAAAAAGATGAAAAATCTGCTTAC ATAGGTTTTGAACCAAGTGGTAAAATACATTTAGGGCATTATCTCCAA ATAAAAAAGATGATTGATTTACAAAATGCTGGATTTGATATAATTATA TTGTTGGCTGATTTACACGCCTATTTAAACCAGAAGGAGAGTTGGAT GAGATTAGAAAAATAGGAGATTATAACAAAAAAGTTTTTGAAGCAATG GGGTTAAAGGCAAAATATGTTTATGGAAGTGAATTCCAGCTTGATAAG GATTATACACTGAATGTCTATAGATTGGCTTTAAAAACTACCTTAAAA AGAGCAAGAAGGAGTATGGAACTTATAGCAAGAGAGGATGAAATCCA AAGGTTGCTGAAGTTATCTATCCAATAATGCAGGTTAATGATATTCAT TATTTAGGCGTTGATGTTGCAGTTGGAGGGATGGAGCAGAGAAAAATA CACATGTTAGCAAGGGAGCTTTTACCAAAAAAGGTTGTTTGTATTCAC AACCCTGTCTTAACGGGTTTGGATGGAGAAGGAAAGATGAGTTCTTCA AAAGGGAATTTTATAGCTGTTGATGACTCTCCAGAAGAGATTAGGGCT AAGATAAAGAAAGCATACTGCCCAGCTGGAGTTGTTGAAGGAAATCCA ATAATGGAGATAGCTAAATACTTCCTTGAATATCCTTTAACCATAAAA AGGCCAGAAAAATTTGGTGGAGATTTGACAGTTAATAGCTATGAGGAG TTAGAGAGTTTATTTAAAAATAAGGAATTGCATCCAATGGATTTAAAA AATGCTGTAGCTGAAGAACTTATAAAGATTTTAGAGCCAATTAGAAAG AGATTA |
| 4 | *p*-azido-L-phenylalanine aminoacyl-tRNA synthetase clone-1 amino acid sequence (derived from wild-type *Methanococcus jannaschii* tyrosyl tRNA-synthetase) | MDEFEMIKRNTSEIISEEELREVLKKDEKSATIGFEPSGKIHL GHYLQIKKMIDLQNAGFDIIILLADLHAYLNQKGELDEIRKIG DYNKKVFEAMGLKAKYVYGSNFQLDKDYTLNVYRLALKTTLKR ARRSMELIAREDENPKVAEVIYPIMQVNPLHYQGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKR PEKFGGDLTVNSYEELESLFKNKELHPMDLKNAVAEELIKILE PIRKRL |
| 5 | *p*-azido-L-phenylalanine aminoacyl-tRNA synthetase clone-2 amino acid sequence (derived from wild-type *Methanococcus jannaschii* tyrosyl tRNA-synthetase) | MDEFEMIKRNTSEIISEEELREVLKKDEKSATIGFEPSGKIHL GHYLQIKKMIDLQNAGFDIIILLADLHAYLNQKGELDEIRKIG DYNKKVFEAMGLKAKYVYGSSFQLDKDYTLNVYRLALKTTLKR ARRSMELIAREDENPKVAEVIYPIMQVNPSHYQGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKR PEKFGGDLTVNSYEELESLFKNKELHPMDLKNAVAEELIKILE PIRKRL |

Fig. 1

| SEQ ID NO: | Description | SEQUENCE |
|---|---|---|
| 6 | p-azido-L-phenylalanine aminoacyl-tRNA synthetase clone-3 amino acid sequence (derived from wild-type *Methanococcus jannaschii* tyrosyl tRNA-synthetase) | MDEFEMIKRNTSEIISEEELREVLKKDEKSATIGFEPSGKIHL GHYLQIKKMIDLQNAGFDIIILLADLHAYLNQKGELDEIRKIG DYNKKVFEAMGLKAKYVYGSSFQLDKDYTLNVYRLALKTTLKR ARRSMELIAREDENPKVAEVIYPIMQVNPLHYQGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKR PEKFGGDLTVNSYEELESLFKNKELHPMDLKNAVAEELIKILE PIRKRL |
| 7 | p-azido-L-phenylalanine aminoacyl-tRNA synthetase clone-4 amino acid sequence (derived from wild-type *Methanococcus jannaschii* tyrosyl tRNA-synthetase) | MDEFEMIKRNTSEIISEEELREVLKKDEKSALIGFEPSGKIHL GHYLQIKKMIDLQNAGFDIIILLADLHAYLNQKGELDEIRKIG DYNKKVFEAMGLKAKYVYGSTFQLDKDYTLNVYRLALKTTLKR ARRSMELIAREDENPKVAEVIYPIMQVNPVHYQGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKR PEKFGGDLTVNSYEELESLFKNKELHPMDLKNAVAEELIKILE PIRKRL |
| 8 | p-azido-L-phenylalanine aminoacyl-tRNA synthetase clone-5 amino acid sequence (derived from wild-type *Methanococcus jannaschii* tyrosyl tRNA-synthetase) | MDEFEMIKRNTSEIISEEELREVLKKDEKSAAIGFEPSGKIHL GHYLQIKKMIDLQNAGFDIIILLADLHAYLNQKGELDEIRKIG DYNKKVFEAMGLKAKYVYGSRFQLDKDYTLNVYRLALKTTLKR ARRSMELIAREDENPKVAEVIYPIMQVNVIHYDGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKR PEKFGGDLTVNSYEELESLFKNKELHPMDLKNAVAEELIKILE PIRKRL |
| 9 | p-azido-L-phenylalanine aminoacyl-tRNA synthetase clone-6 amino acid sequence (derived from wild-type *Methanococcus jannaschii* tyrosyl tRNA-synthetase) | MDEFEMIKRNTSEIISEEELREVLKKDEKSAGIGFEPSGKIHL GHYLQIKKMIDLQNAGFDIIILLADLHAYLNQKGELDEIRKIG DYNKKVFEAMGLKAKYVYGSTFQLDKDYTLNVYRLALKTTLKR ARRSMELIAREDENPKVAEVIYPIMQVNTYYYLGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKR PEKFGGDLTVNSYEELESLFKNKELHPMDLKNAVAEELIKILE PIRKRL |
| 10 | p-azido-L-phenylalanine aminoacyl-tRNA synthetase clone-7 amino acid sequence (derived from wild-type *Methanococcus jannaschii* tyrosyl tRNA-synthetase) | MDEFEMIKRNTSEIISEEELREVLKKDEKSALIGFEPSGKIHL GHYLQIKKMIDLQNAGFDIIILLADLHAYLNQKGELDEIRKIG DYNKKVFEAMGLKAKYVYGSPFQLDKDYTLNVYRLALKTTLKR ARRSMELIAREDENPKVAEVIYPIMQVNQIHSSGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKR PEKFGGDLTVNSYEELESLFKNKELHPMDLKNAVAEELIKILE PIRKRL |
| 11 | pIII fusion streptavidin binding peptide (SBP) | AGXTLLAHPQ |
| 12 | FT18 PCR primmer | GACAGCTTATCATCGATGAGACGTTGATCGGCACGTAAG |
| 13 | FT19 PCR primer | GGTTGGTTTGCGCATTCAGCGCTAACCGTTTTTATCAGGC |
| 14 | FT121 primer | CATGCCCGGGTACCTTTCTATTCTC |
| 15 | FT126 template | CATGTTTCGGCCGAGCCCCCACCCTGCGGATGAGCCAGC AAAGTCTAGCCGGCAGAGTGAGAATAGAAAGGTACCCGG G |

Fig. 1 (cont.)

| *Methanococcus jannaschii* tyrosyl-tRNA synthetase[a] | Amino acid position | | | | | |
|---|---|---|---|---|---|---|
| | 32 | 107 | 158 | 159 | 162 | SEQ ID NO: |
| wild-type | Tyr | Glu | Asp | Ile | Leu | 2 |
| Clone 1 | Thr | Asn | Pro | Leu | Gln | 4 |
| Clone 2 | Thr | Ser | Pro | Ser | Gln | 5 |
| Clone 3 | Thr | Ser | Pro | Leu | Gln | 6 |
| Clone 4 | Leu | Thr | Pro | Val | Gln | 7 |
| Clone 5 | Ala | Arg | Val | Ile | Asp | 8 |
| Clone 6[b] | Gly | Thr | Thr | Tyr | Leu | 9 |
| Clone 7[c] | Leu | Pro | Gln | Ile | Ser | 10 |

(a) All proteins have an $IC_{50}$ of chloramphenicol resistance to 110 mg/L with 1 mM *p*-azido-L-phenylalanine and less than 5 mg/L in the absence of added *p*-azido-L-phenylalanine.
(b) Synthetase clone 6 contains the additional mutation His160Tyr.
(c) Synthetase clone 7 contains the additional mutation Tyr161Ser.

Fig. 2

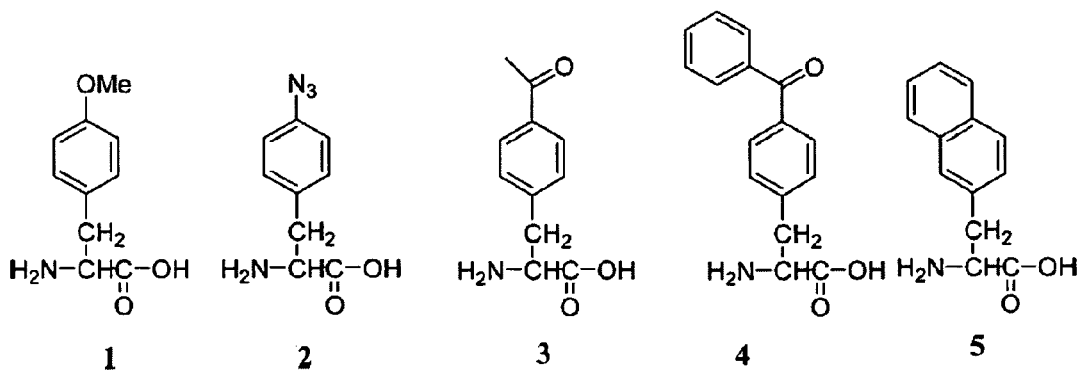

| | Unnatural Amino Acid |
|---|---|
| 1 | O-methyl-tyrosine |
| 2 | *p*-azido-L-phenylalanine |
| 3 | *p*-acetyl-L-phenylalanine |
| 4 | *p*-benzoyl-L-phenylalanine |
| 5 | 3-(2-naphthyl)alanine |

Fig. 3

| M13KE-SBP phage yield ** | Unnatural Amino Acid | | | | |
|---|---|---|---|---|---|
| | 1 | 2 | 3 | 4 | 5 |
| without unnatural amino acid | $1.6 \times 10^9$ ** | $8 \times 10^8$ | $2.2 \times 10^9$ | $1.0 \times 10^9$ | $1.4 \times 10^9$ |
| with unnatural amino acid | $1.2 \times 10^{11}$ | $1.0 \times 10^{11}$ | $1.8 \times 10^{11}$ | $1.6 \times 10^{11}$ | $2.0 \times 10^{11}$ |
| ratio | 75 | 125 | 81 | 160 | 143 |
| ** phage yields expressed at PFU/mL | | | | | |

Fig. 4

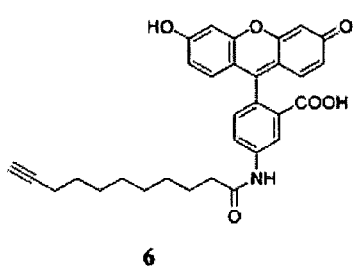

Fig. 5

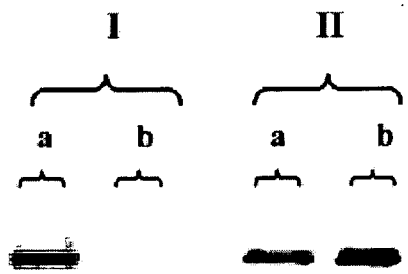

Fig. 6

| Phage Titer | Log(phage) | M13KE-SBP prepared with 3 | M13KE-SBP prepared with 2 | M13KE-SBP prepared in XL1-Blue | M13KE |
|---|---|---|---|---|---|
| $4.00 \times 10^{11}$ | 11.60206 | 0.557867 | 0.584467 | 0.501433 | 0.066867 |
| $1.00 \times 10^{11}$ | 11 | 0.579167 | 0.591133 | 0.4157 | 0.051933 |
| $2.50 \times 10^{10}$ | 10.39794 | 0.604267 | 0.600567 | 0.3675 | 0.0497 |
| $6.25 \times 10^9$ | 9.79588 | 0.590233 | 0.560167 | 0.342333 | 0.049467 |
| $1.56 \times 10^9$ | 9.19382 | 0.475633 | 0.4354 | 0.271367 | 0.048867 |
| $3.91 \times 10^8$ | 8.59176 | 0.359167 | 0.2899 | 0.2061 | 0.0501 |
| $9.77 \times 10^7$ | 7.9897 | 0.168633 | 0.110067 | 0.105333 | 0.049567 |
| $2.44 \times 10^7$ | 7.38764 | 0.067733 | 0.056433 | 0.0587 | 0.049033 |
| Absorbance at 492 nm | | | | | |

Fig. 7

| | Input (PFU) | Output (PFU) | Recovery Rate |
|---|---|---|---|
| M13KE WT | $5.4 \times 10^{10}$ | $3 \times 10^4$ | $1/1.8 \times 10^6$ |
| M13KE-SBP | $1.6 \times 10^{10}$ | $7.5 \times 10^7$ | $1/2.1 \times 10^2$ |
| Enrichment | | | $9.0 \times 10^3$ |

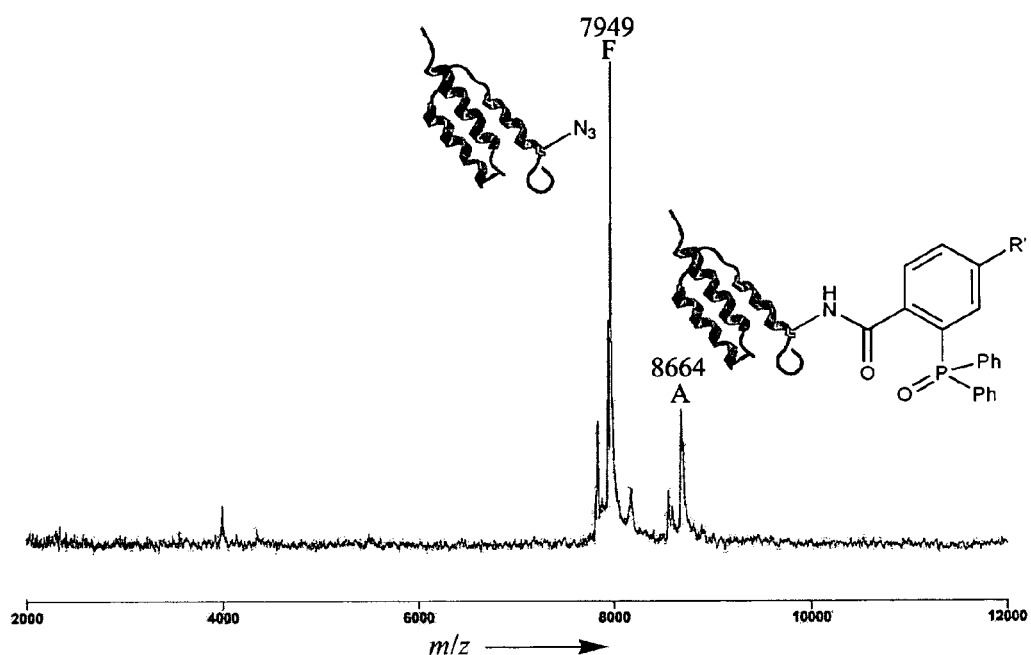
Fig. 14
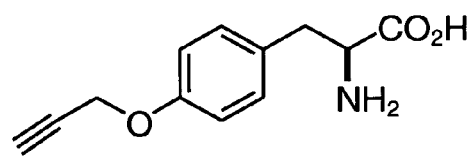
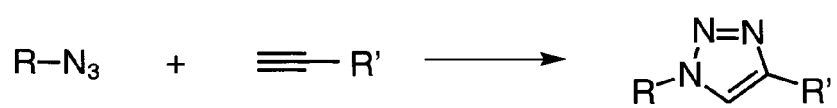
Fig. 15

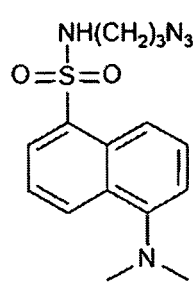
10
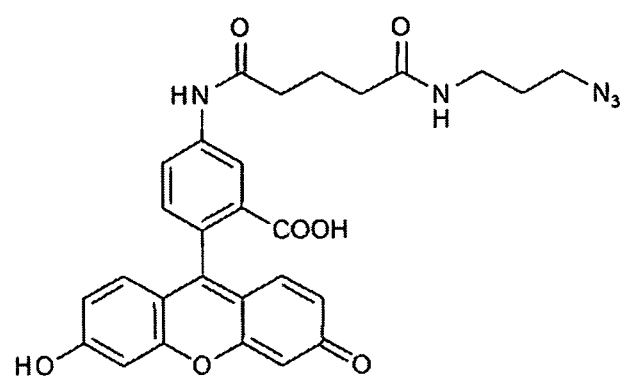
11
Fig. 16

SELECTIVE POSTTRANSLATIONAL MODIFICATION OF PHAGE-DISPLAYED POLYPEPTIDES

CROSS-REFERENCE TO RELATED APPLICATION

This application claims priority to and benefit of U.S. Provisional Patent Application Ser. No. 60/726,137, filed on Oct. 12, 2005, and Provisional Patent Application Ser. No. 60/737,622, filed on Nov. 16, 2005, the contents of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with government support from the Department of Energy under Grant No. ER46051, and the National Institutes of Health under Grant No. GM56528. The government may have certain rights to this invention.

FIELD OF THE INVENTION

The invention relates to the field of protein chemistry, e.g., translation biochemistry. The invention relates to compositions and methods for making bacteriophage, where the phage comprise a displayed polypeptide having an unnatural amino acid that can serve as a target for selective covalent posttranslational modification, resulting in a posttranslationally modified phage.

BACKGROUND OF THE INVENTION

The study of protein structure and function has historically relied upon the reaction chemistries that are available using the reactive groups of the naturally occurring amino acids. Unfortunately, every known organism, from bacteria to humans, encodes the same twenty common amino acids (with the rare exceptions of selenocysteine (see, e.g., A. Bock et al., (1991), *Molecular Microbiology* 5:515-20) and pyrrolysine (see, e.g., G. Srinivasan, et al., (2002), *Science* 296:1459-62). This limited selection of R-groups has restricted the study of protein structure and function, where the studies are confined by the chemical properties of the naturally occurring amino acids.

The limiting number of natural amino acids restricts the ability to make highly targeted posttranslational protein modifications to the exclusion of all other amino acids in a protein. Most modification reactions currently used in the art involve covalent bond formation between nucleophilic and electrophilic reaction partners that target the naturally occurring nucleophilic residues in the protein amino acid side chains, e.g., the reaction of α-halo ketones with histidine or cysteine side chains. Selectivity in these cases is determined by the number and accessibility of the nucleophilic residues in the protein. Unfortunately, naturally occurring proteins frequently contain poorly positioned (e.g., inaccessible) reaction sites or multiple reaction targets (e.g., lysine, histidine and cysteine residues), resulting in poor selectivity in the modification reactions, making highly targeted protein modification by nucleophilic/electrophilic reagents difficult. Furthermore, the sites of modification are typically limited to the naturally occurring nucleophilic side chains of lysine, histidine or cysteine. Modification at other sites is difficult or impossible.

Alternative approaches for selectively modifying proteins with synthetic agents and probes, and covalent attachment of proteins to surfaces have been attempted. These include semi-synthesis (Muir, *Annu. Rev. Biochem.* 2003, 72, 249-289), the use of electrophilic reagents that selectively label cysteine and lysine residues (Chilkoti et al., *Bioconjugate Chem.* 1994, 5, 504-507; Rosendahl et al., *Bioconjugate Chem.* 2005, 16, 200-207), and the selective introduction of amino acids with reactive side chains into proteins by in vitro biosynthesis with chemically aminoacylated tRNAs (Bain et al., *J. Am. Chem. Soc.* 1989, 111, 8013-8014; Ellman et al., *Methods Enzymol.* 1991, 202, 301-336). Each of these approaches suffers from either a lack of target specificity or other impracticalities.

One strategy to overcome the limitations of the existing genetic repertoire is to add amino acids that have distinguishing chemical properties to the genetic code. This approach has proven feasible using orthogonal tRNA molecules and corresponding novel orthogonal aminoacyl-tRNA synthetases to add unnatural amino acids to proteins using the in vivo protein biosynthetic machinery of a host cell, e.g., the eubacteria *Escherichia coli* (*E. coli*). This approach is described in various sources, for example, Chin et al., *Science* (2003) 301:964-967; Zhang et al., *Proc. Natl. Acad. Sci. U.S.A.* 2004, 101:8882-8887; Anderson et al., *Proc. Natl. Acad. Sci. U.S.A.* 2004, 101:7566-7571; Wang et al., (2001) *Science* 292:498-500; Chin et al., (2002) *Journal of the American Chemical Society* 124:9026-9027; Chin and Schultz, (2002) *ChemBioChem* 11:1135-1137; Chin, et al., (2002) *PNAS United States of America* 99:11020-11024; Wang and Schultz, (2002) *Chem. Comm.*, 1-10; Wang and Schultz "Expanding the Genetic Code," *Angewandte Chemie Int. Ed.*, 44(1):34-66 (2005); and Xie and Schultz, "An Expanding Genetic Code," *Methods* 36:227-238 (2005). See also, International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO2005/007870, filed Jul. 7, 2004; WO 2005/007624, filed Jul. 7, 2004; and International Publication No. WO2006/034332, filed on Sep. 20, 2005.

Phage display technology is a malleable and widely utilized technique that has found applications in diverse biological disciplines. See, e.g., Smith and Petrenko, *Chem. Rev.*, 97:391-410 (1997); Sidhu, *Bimolecular Engineering* 18:57-63 (2001); Rodi and Makowski, *Current Opinion in Biotechnology* 10:87-93 (1999); and Willats, *Plant Molecular Biology* 50:837-854 (2002). For example, phage display has proven very useful for the isolation of high-affinity ligands and receptors from large polypeptide libraries. It has the advantages that large libraries can be easily generated by recombinant methods, library members can be amplified for iterative rounds of enrichment, and primary structure can be determined by DNA sequencing. However, like proteins in general, phage-displayed peptide libraries are also restricted to the common 20 amino acid building blocks, limiting the functional groups that can be targeted for posttranslational modification. Moreover, methods for posttranslational modification of phage-displayed polypeptides, where the modification reaction uses physiologically-compatible conditions that preserve protein activity and phage viability present even greater challenge (Leieux and Bertozzi (1998) *TIBTECH*, 16:506).

In an attempt to expand the scope of phage-display utility, Noren and co-workers incorporated selenocysteine into phage displayed peptides using a natural selenocysteine opal suppressing tRNA (Sandman et al., *J. Am. Chem. Soc.* (2000) 122:960-961). Roberts et al. attempted to generalize this approach to peptide libraries containing other unnatural amino acids using in vitro mRNA display (Li et al., *J. Am. Chem. Soc.*, (2002) 124:9972) with chemically aminoacylated amber suppressor tRNAs (Noren et al., *Science* (1989) 244:182-188). However, the generation of a large number of such tRNAs is impractical, and they are consumed stoichiometrically.

What is needed in the art are new strategies for incorporation of unnatural amino acids into phage-displayed polypeptides for the purpose of modifying and studying protein structure and function, where the unnatural amino acids in the displayed polypeptides can be selectively targeted for post-translational modification while displayed on the phage. There is a need in the art for the creation of new strategies for protein modification reactions that modify phage-displayed proteins in a highly selective fashion, and furthermore, allow the modification of the phage-displayed proteins under physiological conditions that preserve phage viability following the modification reaction. What is needed in the art are novel methods for producing targeted protein modifications on phage-displayed proteins, where the modifications are highly specific, e.g., modifications where none of the naturally occurring amino acids in the polypeptides are subject to cross reactions or side reactions. The invention described herein fulfills these and other needs, as will be apparent upon review of the following disclosure.

SUMMARY OF THE INVENTION

There is a need for chemical reactions that modify proteins, e.g., phage-displayed proteins, in a highly selective fashion. Most reactions currently used in the art for the selective modification of proteins have poor selectivity and are limited to naturally occurring amino acid residues. The present invention provides solutions to these problems.

The invention provides systems for the programmed, site-specific biosynthetic incorporation of unnatural amino acids into phage-displayed proteins by manipulating orthogonal translation systems to work in conjunction with recombinant phage expression reagents. The invention provides methods for the subsequent targeted modification of those unnatural amino acid residues that are incorporated into phage-displayed polypeptides. The invention provides novel compositions (e.g., phage comprising various posttranslational modifications) and novel methods for the generation of post-translationally modified phage.

The phage-production systems provided herein take advantage of orthogonal translation systems that use *E. coli* host cells for the selective incorporation of unnatural amino acids into phage-displayed polypeptides, and the subsequent modification of those polypeptides using selective modification of the unnatural amino acid residue. Various chemistries for the modification of the unnatural amino acid residue in the phage-displayed polypeptide are demonstrated, including [3+2] cycloaddition reactions and Staudinger ligations. The nature of the material that is conjugated to the phage-displayed protein via an unnatural amino acid target is not particularly limited and can be any desired entity.

The invention provides phage having a displayed fusion polypeptide, where the polypeptide comprises at least one post-translationally modified unnatural amino acid residue. A variety of reactive unnatural amino acids can be used in the displayed polypeptide. For example, the unnatural amino acid can be an aryl-azide unnatural amino acid (e.g., para-azido-L-phenylalanine) or an alkynyl unnatural amino acid (e.g., para-propargyloxyphenylalanine). The phage can be a filamentous phage, e.g., an M13-derived phage.

The displayed polypeptide is generally a fusion polypeptide that comprises a phage capsid protein (or a portion or variant thereof) and an amino acid sequence of interest. In some embodiments, the fusion polypeptide is designed to incorporate a peptide linker protease recognition sequence specifically cleavable by a site-specific protease, e.g., Factor Xa, Factor XIa, Kallikvein, thrombin, Factor XIIa, collagenase or enterokinase.

Various types of modification reactions are employed for the modification of the phage-displayed polypeptide having the unnatural amino acid. For example, an azide-alkyne [3+2] cycloaddition reaction (which produces a triazole linkage) or a Staudinger ligation reaction can be used. Because of the unique reaction chemistries of aryl-azide and alkynyl unnatural amino acids, phage-displayed proteins into which they are incorporated can be modified with extremely high selectivity. In some cases, the unnatural amino acid reactive group has the advantage of being completely alien to in vivo systems, thereby improving reaction selectivity. Advantageously, use of the Staudinger reaction preserves viral infectivity.

The modified phage of the invention can optionally be immobilized to a solid support. In some embodiments, the phage comprise a phage polypeptide library, where a plurality of polypeptides are expressed by the phage. This plurality of phage is also a feature of the invention. The phage of the invention can be purified or isolated In other embodiments, the invention provides methods for the production of the aforementioned post-translationally modified phages. Generally, these methods have the steps of (a) providing a phage comprising a displayed polypeptide comprising at least one unnatural amino acid residue that is an aryl-azide unnatural amino acid residue (e.g., para-azido-L-phenylalanine) or an alkynyl unnatural amino acid residue (e.g., para-propargyloxyphenylalanine); and (b) reacting the phage under conditions wherein the unnatural amino acid residue undergoes covalent modification, thereby producing a post-translationally modified phage. These modification reactions can use an azide-alkyne [3+2] cycloaddition reaction or a Staudinger ligation reaction. When the Staudinger modification reaction is used, the resulting modified phage can be viable virion.

More specifically, providing the unmodified phage can have the following steps: (i) providing a eubacterial host cell that comprises (A) a nucleic acid molecule encoding the phage, where the polynucleotide portion that encodes the fusion polypeptide of interest comprises at least one selector codon; (B) a nucleic acid molecule encoding an aminoacyl-tRNA synthetase that is orthogonal in said host cell (O-RS); (C) a nucleic acid molecule encoding a tRNA that is orthogonal in the host cell (O-tRNA), wherein the O-RS preferentially aminoacylates the O-tRNA with the unnatural amino acid in the host cell and where said selector codon is recognized by the O-tRNA; and D) an aryl-azide or an alkynyl unnatural amino acid; and (ii) culturing the host cell, thereby producing a polypeptide encoded by said polynucleotide subsequence, where an aryl-azide or an alkynyl unnatural amino acid is incorporated into the polypeptide during translation in response to the selector codon, and producing a phage comprising a polypeptide encoded by said polynucleotide subsequence, where an aryl-azide or an alkynyl unnatural amino acid is incorporated into said polypeptide. In some aspects, an *E. coli* host cell is also provided.

The orthogonal tRNA and synthetase that are used in the methods is not particularly limiting. In some embodiments, the host cell comprises a nucleic acid molecule that encodes an O-RS derived from a *Methanococcus jannaschii* aminoacyl-tRNA synthetase, e.g., a *Methanococcus jannaschii* tyrosyl-tRNA synthetase. In some embodiments, the O-tRNA used is an amber suppressor tRNA.

In still other embodiments, it is further contemplated that additional unnatural amino acids can be used to target phage for post-translational modifications, where the unnatural amino acid is incorporated into the phage by using an orthogonal translation system comprising a suppressor tRNA and mutant synthetase.

In some aspects, any phage comprising a polypeptide that comprises at least one post-translationally modified unnatural amino acid residue is a phage of the invention, where the at least one unnatural amino acid allows for targeted covalent modification. In some aspects, the phage are viable following post-translational modification. Reactive amino acids that can be incorporated into phage in this manner can include para-propargyloxyphenylalanine, para-azido-L-phenylalanine, para-acetyl-L-phenylalanine, meta-acetyl-L-phenylalanine, para-(3-oxobutanoyl)-L-phenylalanine, para-(2-amino-1-hydroxyethyl)-L-phenylalanine, para-isopropylthiocarbonyl-L-phenylalanine and para-ethylthiocarbonyl-L-phenylalanine.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes combinations of two or more cells; reference to "a polynucleotide" includes, as a practical matter, many copies of that polynucleotide.

Unless defined herein and below in the reminder of the specification, all technical and scientific terms used herein have the same meaning as commonly understood by one of ordinary skill in the art to which the invention pertains.

Orthogonal: As used herein, the term "orthogonal" refers to a molecule (e.g., an orthogonal tRNA (O-tRNA) and/or an orthogonal aminoacyl-tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl orthogonal tRNA/RS pair).

Orthogonal tyrosyl-tRNA: As used herein, an orthogonal tyrosyl-tRNA (tyrosyl-O-tRNA) is a tRNA that is orthogonal to a translation system of interest, where the tRNA is: (1) identical or substantially similar to a naturally occurring tyrosyl-tRNA, (2) derived from a naturally occurring tyrosyl-tRNA by natural or artificial mutagenesis, (3) derived by any process that takes a sequence of a wild-type or mutant tyrosyl-tRNA sequence of (1) or (2) into account, (4) homologous to a wild-type or mutant tyrosyl-tRNA; (5) homologous to any example tRNA that is designated as a substrate for a tyrosyl-tRNA synthetase in FIG. 1 or 2, or (6) a conservative variant of any example tRNA that is designated as a substrate for a tyrosyl-tRNA synthetase in FIG. 1 or 2. The tyrosyl-tRNA can exist charged with an amino acid, or in an uncharged state. It is also to be understood that a "tyrosyl-O-tRNA" optionally is charged (aminoacylated) by a cognate synthetase with an amino acid other than tyrosine or leucine, respectively, e.g., with an unnatural amino acid. Indeed, it will be appreciated that a tyrosyl-O-tRNA of the invention is advantageously used to insert essentially any amino acid, whether natural or artificial, into a growing polypeptide, during translation, in response to a selector codon.

Orthogonal tyrosyl amino acid synthetase: As used herein, an orthogonal tyrosyl amino acid synthetase (tyrosyl-O-RS) is an enzyme that preferentially aminoacylates the tyrosyl-O-tRNA with an amino acid in a translation system of interest. The amino acid that the tyrosyl-O-RS loads onto the tyrosyl-O-tRNA can be any amino acid, whether natural, unnatural or artificial, and is not limited herein. The synthetase is optionally the same as or homologous to a naturally occurring tyrosyl amino acid synthetase, or the same as or homologous to a synthetase designated as an O-RS in FIG. 1 or 2 (see, SEQ ID NOS: 4-10). For example, the O-RS can be a conservative variant of a tyrosyl-O-RS of FIG. 1, and/or can be at least 50%, 60%, 70%, 80%, 90%, 95%, 98%, 99% or more identical in sequence to an O-RS of FIG. 1.

Cognate: The term "cognate" refers to components that function together, e.g., an orthogonal tRNA and an orthogonal aminoacyl-tRNA synthetase. The components can also be referred to as being complementary.

Preferentially aminoacylates: As used herein in reference to orthogonal translation systems, an O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon (e.g., an amber, ocher or opal codon), a four base codon, a rare codon, etc.

Suppression activity: As used herein, the term "suppression activity" refers, in general, to the ability of a tRNA (e.g., a suppressor tRNA) to allow translational read-through of a codon (e.g., a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

The present invention provides various methods by which suppression activity can be quantitated. Percent suppression of a particular O-tRNA and O-RS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a "background" or "negative" control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatived lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a non-eukaryotic cell, e.g., a bacterium (such as *E. coli*), or in a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analogue, that is not one of the 20 common naturally occurring amino acids or seleno cysteine or pyrrolysine. For example, the unnatural amino acid p-azido-L-phenylalanine finds use with the invention.

Derived from: As used herein, the term "derived from" refers to a component that is isolated from or made using a specified molecule or organism, or information from the specified molecule or organism. For example, a polypeptide that is derived from a second polypeptide caninclude an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random, or a mixture of each. The mutagenesis of a polypepitde to create a different polypeptide derived from the first can be a random event (e.g., caused by polymerase infidelity) and the identification of the derived polypeptide can be made by appropriate screening methods, e.g., as discussed herein. Mutagenesis of a polypeptide typically entails manipulation of the polynucleotide that encodes the polypeptide.

Positive selection or screening marker: As used herein, the term "positive selection or screening marker" refers to a marker that, when present, e.g., expressed, activated or the like, results in identification of a cell, which comprises the trait, e.g., a cell with the positive selection marker, from those without the trait.

Negative selection or screening marker: As used herein, the term "negative selection or screening marker" refers to a marker that, when present, e.g., expressed, activated, or the like, allows identification of a cell that does not comprise a selected property or trait (e.g., as compared to a cell that does possess the property or trait).

Reporter: As used herein, the term "reporter" refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/lacZ (β-galactosidase), ADH (alcohol dehydrogenase), his3, ura3, leu2, lys2, or the like.

Eukaryote: As used herein, the term "eukaryote" refers to organisms belonging to the Kingdom Eucarya. Eukaryotes are generally distinguishable from prokaryotes by their typically multicellular organization (but not exclusively multicellular, for example, yeast), the presence of a membrane-bound nucleus and other membrane-bound organelles, linear genetic material (i.e., linear chromosomes), the absence of operons, the presence of introns, message capping and poly-A mRNA, and other biochemical characteristics, such as a distinguishing ribosomal structure. Eukaryotic organisms include, for example, animals (e.g., mammals, insects, reptiles, birds, etc.), ciliates, plants (e.g., monocots, dicots, algae, etc.), fungi, yeasts, flagellates, microsporidia, protists, etc.

Prokaryote: As used herein, the term "prokaryote" refers to organisms belonging to the Kingdom Monera (also termed Procarya). Prokaryotic organisms are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma are sometimes given separate classifications under the Kingdom Monera.

Bacteria: As used herein, the terms "bacteria" and "eubacteria" refer to prokaryotic organisms that are distinguishable from Archaea. Similarly, Archaea refers to prokaryotes that are distinguishable from eubacteria. Eubacteria and Archaea can be distinguished by a number morphological and biochemical criteria. For example, differences in ribosomal RNA sequences, RNA polymerase structure, the presence or absence of introns, antibiotic sensitivity, the presence or absence of cell wall peptidoglycans adn other cell wall components, the branched versus unbranched structures of membrane lipids, and the presence/absence of histones and histone-like proteins are used to assign an organism to Eubacteria or Archaea.

Examples of Eubacteria include *Escherichia coli, Thermus therinophilus* and *Bacillus stearothermophilus*. Example of Archaea include *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species *NRC-1, Archaeoglobus fulgidus* (Af), *Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thermoplasma acidophilum* and *Thermoplasma volcanium*.

Conservative variant: As used herein, the term "conservative variant," in the context of a translation component, refers to a translation component, e.g., a conservative variant O-tRNA or a conservative variant O-RS, that functionally performs similar to a base component that the conservative variant is similar to, e.g., an O-tRNA or O-RS, having variations in the sequence as compared to a reference O-tRNA or O-RS. For example, an O-RS, or a conservative variant of that O-RS, will aminoacylate a cognate O-tRNA with an unnatural amino acid, e.g., an amino acid comprising an N-acetylgalactosamine moiety. In this example, the O-RS and the conservative variant O-RS do not have the same amino acid sequences. The conservative variant can have, e.g., one variation, two variations, three variations, four variations, or five or more variations in sequence, as long as the conservative variant is still complementary to the corresponding O-tRNA or O-RS.

In some embodiments, a conservative variant O-RS comprises one or more conservative amino acid substitutions compared to the O-RS from which it was derived. In some embodiments, a conservative variant O-RS comprises one or more conservative amino acid substitutions compared to the O-RS from which it was derived, and furthermore, retains O-RS biological activity; for example, a conservative variant O-RS that retains at least 10% of the biological activity of the parent O-RS molecule from which it was derived, or alternatively, at least 20%, at least 30%, or at least 40%. In some preferred embodiments, the conservative variant O-RS retains at least 50% of the biological activity of the parent O-RS molecule from which it was derived. The conservative amino acid substitutions of a conservative variant O-RS can occur in any domain of the O-RS, including the amino acid binding pocket.

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

In response to: As used herein, the term "in response to" refers to the process in which an O-tRNA of the invention recognizes a selector codon and mediates the incorporation of the unnatural amino acid, which is coupled to the tRNA, into the growing polypeptide chain.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

Azido: As used herein, the term "azido" refers to the chemical group —N$_3$, typically attached to a carbon atom, having the general structure:

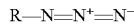

For example, the unnatural amino acid p-azido-L-phenylalanine (FIG. 3, structure 2) comprises an azido moiety. Also, an azido dye is a dye molecule with an azido substituent group (see, e.g., the azido dyes 10 and 11, in FIG. 16). The term "azide" refers to a chemical compound containing the azido group (for example, benzyl azide, sodium azide, etc.). An aryl-azide is a aromatic molecule comprising an azide moiety, e.g., the unnatural amino acid p-azido-L-phenylalanine is an aryl-azide.

Alkyne: As used herein, the term "alkyne" (also sometimes referred to as "acetylene") refers to chemical structures containing a triple bond between two carbon atoms, having the general structure:

where R is any atom or structure. When used as a substituent, the alkyne moiety is termed an "alkynyl" group. The alkynyl carbon atoms are sp$^2$ hybridized and form only bonds to two other atoms; one of these bonds will be a single bond while the second bond is a triple bond. For example, the amino acid para-propargyloxyphenylalanine (pPRO-Phe) comprises an alkynyl group See, FIG. 15, structure 9. Because alkynyl substituents do not appear on amino acids in nature, any alkynyl amino acid is an unnatural amino acid. Also, FIG. 5, structure 6, provides the chemical structure of an alkyne-derivatized fluorescein dye.

Polypeptide: A polypeptide is any oligomer of amino acids (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell or translation system, or a polypeptide produced by cell-free synthetic means. A polypeptide is characterized by its amino acid sequence, e.g., the primary structure of its component amino acids. As used herein, the amino acid sequence of a polypeptide is not limited to full-length sequences, but can be partial or complete sequences. Furthermore, it is not intended that a polypeptide be limited by possessing or not possessing any particular biological activity. As used herein, the term "protein" is synonymous with polypeptide. The term "peptide" refers to a small polypeptide, for example but not limited to, from 2-25 amino acids in length.

Posttranslational modification: As used herein, a posttranslational modification is a modification to a polypeptide that can occur within a cell or in a cell free-system, either cotranslationally or after the polypeptide has been fully translated. Post-translational modifications can be naturally occurring in vivo, and in many instances are required in order for a native polypeptide to be biologically active. A wide variety of post-translational modifications are known to exist in vivo, including, e.g., glycosylation and/or phosphorylation, and are typically regulated by endogenous cellular components such as cellular proteins. A polypeptide can be subject to multiple types of posttranslational modifications and the modifications can be anywhere within the polypeptide molecule.

Known posttranslational modifications include, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature, such as, for instance, Creighton, T. E., Proteins—Structure And Molecular Properties, 2nd Ed., W.H. Freeman and Company, New York (1993); Wold, F., "Posttranslational Protein Modifications: Perspectives and Prospects," in Post-translational Covalent Modification of Proteins, Johnson, B. C., ed., Academic Press, New York (1983), pp. 1-12; Seifter et al., "Analysis for protein modifications and nonprotein cofactors," *Meth. Enzymol.* 182:626-646 (1990), and Rattan et al., Ann. N.Y Acad. Sci. 663:48-62 (1992).

Solid support: As used herein, the term "solid support" refers to a matrix of material in a substantially fixed arrangement that can be functionalized to allow synthesis, attachment or immobilization of polypeptides (e.g., or phage comprising polypeptides), either directly or indirectly. The term "solid support" also encompasses terms such as "resin" or "solid phase." A solid support can be composed of polymers, e.g., organic polymers such as polystyrene, polyethylene, polypropylene, polyfluoroethylene, polyethyleneoxy, and polyacrylamide, as well as co-polymers and grafts thereof. A solid support can be inorganic, such as glass, silica, silicon, controlled-pore-glass (CPG), reverse-phase silica, or any suitable metal. In addition to those described herein, it is also intended that the term "solid support" include any solid support that has received any type of coating or any other type of secondary treatment, e.g., Langmuir-Blodgett films, self-assembled monolayers (SAM), sol-gel, or the like.

Array: As used herein, "array" or "microarray" is an arrangement of elements (e.g., phage-displayed polypeptides), e.g., present on a solid support and/or in an arrangement of vessels. While arrays are most often thought of as physical elements with a specified spatial-physical relationship, the present invention can also make use of "logical" arrays, which do not have a straightforward spatial organization. For example, a computer system can be used to track the location of one or several components of interest that are located in or on physically disparate components. The computer system creates a logical array by providing a "look-up" table of the physical location of array members. Thus, even components in motion can be part of a logical array, as long as the members of the array can be specified and located. This is relevant, e.g., where the array of the invention is present in a flowing microscale system, or when it is present in one or more microtiter trays.

Certain array formats are sometimes referred to as a "chip" or "biochip." An array can comprise a low-density number of addressable locations, e.g., 2 to about 10, medium-density, e.g., about a hundred or more locations, or a high-density number, e.g., a thousand or more. Typically, the chip array format is a geometrically-regular shape that allows for facilitated fabrication, handling, placement, stacking, reagent introduction, detection, and storage. It can, however, be irregular. In one typical format, an array is configured in a row and column format, with regular spacing between each location of member sets on the array. Alternatively, the locations can be bundled, mixed, or homogeneously blended for equalized treatment or sampling. An array can comprise a plurality of addressable locations configured so that each location is spatially addressable for high-throughput handling, robotic delivery, masking, or sampling of reagents. An array can also be configured to facilitate detection or quantitation by any particular means, including but not limited to, scanning by laser illumination, confocal or deflective light gathering, CCD detection, and chemical luminescence. "Array" formats, as recited herein, include but are not limited to, arrays (i.e., an array of a multiplicity of chips), microchips, microarrays, a microarray assembled on a single chip, arrays of biomolecules attached to microwell plates, or any other appropriate format for use with a system of interest.

Covalent bond: A used herein, a covalent bond is a bond comprising shared electrons between atoms. A covalent bond is synonymous with "chemical bond." A non-covalent bond is any bond that is not a covalent bond. One type of non-covalent bond is an ionic bond. An ionic bond is an attraction between oppositely charged chemical moieties. In an ionic bond, electrons are not shared, but rather, are unequally transferred resulting in unequal charge distributions and positive/negative charge attractions.

BRIEF DESCRIPTION OF THE FIGURES

FIG. 1 provides examples of polynucleotide and polypeptide sequences that find use with the invention.

FIG. 2 provides examples of amino acid sequences of *Methanococcus jannaschii* tyrosyl-tRNA synthetase mutants that have the ability to charge an orthogonal tRNA with the unnatural amino acid para-azido-L-phenylalanine.

FIG. 3 provides the structures and corresponding names of five (numbered 1 through 5) unnatural amino acids, which are O-methyl-tyrosine (1), para-azido-L-phenylalanine (2), para-acetyl-L-phenylalanine (3), para-benzoyl-L-phenylalanine (4) and 3-(2-naphthyl)alanine (5).

FIG. 4 provides the results of an experiment demonstrating the dependence of M13-SBP phage yields (expressed as PFU/mL) on the presence of the corresponding unnatural amino acid.

FIG. 5 provides the chemical structure of an alkyne-derivatized fluorescein dye (structure 6).

FIG. 6 provides a chemiluminescence image following a Western blot analysis using anti-fluorescein (I) or anti-pIII (II) primary antibodies, where the samples constitute reaction material following the [3+2] cycloaddition reactions of M13KE-SBP phage, where the phage are prepared in either the strain TTS/RS in the presence of p-azido-L-phenylalanine 2 (a) or prepared in XL1-Blue (b).

FIG. 7 provides the absorbance value results of a phage streptavidin binding ELISA. Absorbance was measures at 492 nm.

FIG. 14 provides a MALDI-TOF analysis of the reaction products from the Staudinger ligation of p-azido-L-phenylalanine 2 containing Z-domain protein with phosphine 7 and doping with a comparative amount of authentic p-azido-L-phenylalanine 2 Z-domain mutant.

FIG. 15 provides the chemical structure (9) of the unnatural alkynyl amino acid para-propargyloxyphenylalanine (pPRO-Phe; also known as 2-amino-3-[4-(prop-2-ynyloxy)phenyl]-propionic acid according to IUPAC nomenclature). FIG. 15 also provides the generalized reaction chemistry of the irreversible formation of triazole structures by a [3+2] cycloaddition reaction of an azido and an alkyne in the presence of copper at room temperature.

FIG. 16 provides the chemical structures (10 and 11) of two azido-functionalized dyes. Dye 10 contains a dansyl fluorophore, and dye 11 contains a fluorescein fluorophore.

DETAILED DESCRIPTION OF THE INVENTION

Figures 8, 9:
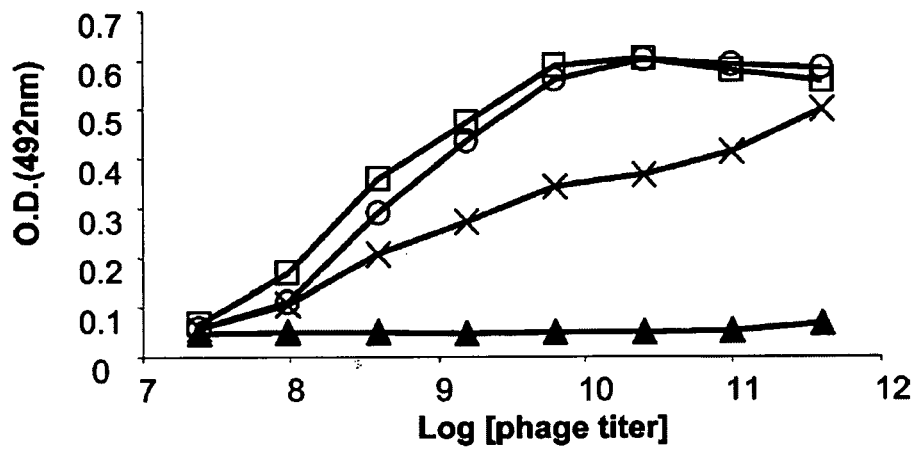
FIG. 8 provides the graphical results of the phage streptavidin binding ELISA shown in FIG. 7. (▲) M13KE; (□) M13KE-SBP phage prepared in strain TTS/RS in the presence of 3; (O) M13KE-SBP phage prepared in TTS/RS in the presence of 2; (x) M13KE-SBP phage prepared in XL1-Blue.
FIG. 9 provides the results of an enrichment factor determination of phage recovery.

There is a need for chemical reactions that modify phage-displayed proteins in a highly selective fashion. There is also a need for such modification reactions that can operate in physiologically-compatible conditions in order to preserve protein activity and phage viability. Most reactions currently used in the art for the selective modification of proteins, e.g., phage-displayed proteins, involve covalent bond formation between nucleophilic and electrophilic reaction partners that target naturally occurring nucleophilic residues in the amino acid side chains. Selectivity in these cases is determined by the number and accessibility of the nucleophilic residues in the protein. Unfortunately, naturally occurring proteins frequently contain poorly positioned (e.g., inaccessible) reaction sites or multiple reaction targets (e.g., lysine, histidine and cysteine residues), resulting in poor selectivity in the modification reactions, making highly targeted protein modification by nucleophilic/electrophilic reagents difficult. Furthermore, the sites of modification are typically limited to the naturally occurring nucleophilic side chains of lysine, histidine or cysteine. Modification at other sites is difficult or impossible.

The present invention provides solutions to these problems. The invention provides systems for the programmed, site-specific biosynthetic incorporation of unnatural amino acids with novel properties into phage-displayed proteins by manipulating orthogonal translation systems to work in conjunction with recombinant phage expression reagents. The invention provides methods for the subsequent targeted modification of those unnatural amino acid residues that are incorporated into phage-displayed polypeptides. We describe herein novel compositions (e.g., phage comprising various posttranslational modifications) and novel methods for the generation of post-translationally modified phage.

The phage-production systems provided by the present invention take advantage of orthogonal translation systems that use $E.$ $coli$ host cells for the selective incorporation of unnatural amino acids into phage-displayed polypeptides, and the subsequent modification of those polypeptides using selective modification of the unnatural amino acid residue. Various chemistries for the modification of the unnatural amino acid residue in the phage-displayed polypeptide are contemplated and demonstrated herein, including [3+2] cycloaddition reactions and Staudinger ligations.

The orthogonal translation systems finding use with the invention comprise an orthogonal tRNA that recognizes a selector codon and an orthogonal aminoacyl-tRNA synthetase that specifically charges the orthogonal tRNA with an unnatural amino acid in $E.$ $coli$ host cells. The incorporation of the unnatural amino acid into the phage-displayed protein of interest can be programmed to occur at any desired position by engineering the polynucleotide encoding the protein of interest to contain the selector codon at the desired site, thereby signaling the incorporation of the unnatural amino acid.

The present disclosure describes the incorporation of a number of unnatural amino acids into phage displayed polypeptides. These amino acids include O-methyl-tyrosine, p-azido-L-phenylalanine, p-acetyl-L-phenylalanine, p-benzoyl-L-phenylalanine and 3-(2-naphthyl)alanine. Aryl-azide amino acids, e.g., para-azido-L-phenylalanine, present attractive targets for specific and regioselective posttranslational modifications. Unnatural amino acids comprising alkynyl-groups, e.g., para-propargyloxyphenylalanine, are also contemplated for use in phage-displayed polypeptides as targets for posttranslational modification. In some embodiments of the invention, the posttranslational modification of the unnatural amino acid in the phage-displayed polypeptide is done using relatively mild and physiologically-compatible in vitro or in vivo reaction conditions that preserve phage viability.

Because of the unique reaction chemistries of aryl-azide and alkynyl unnatural amino acids, phage-displayed proteins into which they are incorporated can be modified with extremely high selectivity. In some cases, the unnatural amino acid reactive group has the advantage of being completely alien to in vivo systems, thereby improving reaction selectivity.

The nature of the material that is conjugated to a phage-displayed protein via an unnatural amino acid target is not particularly limited and can be any desired entity, e.g., dyes, fluorophores, crosslinking agents, saccharide derivatives, polymers (e.g., derivatives of polyethylene glycol), photo-crosslinkers, cytotoxic compounds, affinity labels, derivatives of biotin, resins, beads, a second protein or polypeptide (or more), polynucleotide(s) (e.g., DNA, RNA, etc.), metal chelators, cofactors, fatty acids, carbohydrates, and the like. The disclosure herein describes the experimental use of derivatized fluorescein or dansyl fluorophore dyes as conjugated material. However, it is not intended that the invention be limited to the use of these conjugated materials, as a wide range of conjugatable materials is contemplated, e.g., those listed above.

Phage Display

Phage display technology has become a widely used technique in diverse biological disciplines. Phage display has found particular use in peptide (i.e., polypeptide) library screening protocols. Various applications include affinity selection (e.g., target receptor selection), epitope mapping and mimicking, identification of new receptors and natural ligands, drug discovery, epitope discovery for vaccine development and diagnostics, and study of DNA-binding proteins. A variety of resources are available that describe the many protocols, reagents and variant phage genomes (and variant phage genes) that find use in phage-display technology. See, e.g., Smith and Petrenko, $Chem.$ $Rev.,$ 97:391-410 (1997); Sidhu, $Bimolecular$ $Engineering$ 18:57-63 (2001); Rodi and Makowski, $Current$ $Opinion$ $in$ $Biotechnology$ 10:87-93 (1999); and Willats, $Plant$ $Molecular$ $Biology$ 50:837-854 (2002).

Experiments described in the present disclosure use the filamentous M13KE phage system (New England BioLabs, Inc.). M13KE is a derivative of M13mp19 designed for expression of peptides as N-terminal pIII fusions in phage display applications (Zwick et al. (1998) $Anal.$ $Biochem.,$ 264:87-97). Libraries constructed in M13KE are pentavalent (i.e., all five copies of pIII in the mature virion carry the fused peptide). Relative to the parent M13mp19, Acc65 I/Kpn I and Eag I sites have been introduced flanking the pIII leader peptidase cleavage site, and the Acc65 I/Kpn I site in the multiple cloning site (MCS) was deleted. Phage displayed random peptide libraries are constructed by annealing an extension primer to a synthetic oligonucleotide encoding the random peptide library and a portion of the pIII leader sequence, extending with DNA polymerase, and digesting with Acc65 I and Eag I (Noren and Noren (2001) $Methods$ 23:169-178). The resulting cleaved duplex is inserted into M13KE which has been digested with the same enzymes.

Although the Examples provided herein use the M13KE phage system, it is not intended that the invention be limited to that particular system. Indeed, one of skill in the art recognizes alternative phage display reagents and protocols that are available and also find use with the compositions and methods of the invention. These alternative reagents and protocols do not depart from the scope of the invention, and are encompassed by the claimed invention.

Generally, display of a polypeptide of interest is accomplished by fusing the polypeptide with a phage capsid (coat) protein, or a fragment, mutant or other variant of a capsid protein. These capsid proteins can include pIII, pVI, pVII, pVIII and pIX. For the purpose of demonstrating (but not limiting) the invention, the Examples herein describe the generation of phage-displayed fusion polypeptides comprising the phage pIII coat protein amino acid sequence. It is not intended that the invention be limited to use of the pIII polypeptide sequence for the display of the fused protein of interest.

In some phage systems, a linker protease recognition signal sequence can be engineered into the cased fusion polypeptide, thereby facilitating cleavage and/or release of the fused protein moiety. A wide variety of protease signal sequences are known, including but not limited to Factor Xa, Factor XIa, Kallikvein, thrombin, Factor XIIa, collagenase and enterokinase. Any suitable protease recognition signal and corresponding protease can be used with the present invention.

Similarly, to demonstrate (but not to limit) the present invention, the disclosure herein demonstrates that an unnatural amino acid moiety can be incorporated into a model phage-displayed fusion protein comprising the streptavidin binding peptide (SBP), which is then post-translationally modified. It is not intended that the incorporation of an unnatural amino acid be limited to such a model protein. From the present disclosure, it will be clear that the incorporation of an unnatural amino acid into any given phage-displayed protein of interest is advantageous for a wide variety of proteins for use in therapeutic and research purposes.

The invention also provides phage comprising polypeptides comprising at least one unnatural amino acid that is post-translationally modified, where the phage is purified or isolated. For example, the phage can be purified and/or isolated by PEG precipitation and/or centrifugation. See, Example 3. Additional phage precipitation and purification/isolation techniques are also known in the art, for example, using affinity purification schemes such as immuno-affinity.

Phage Display Libraries and Arrays

The phage display of polypeptides comprising unnatural amino acids that are post-translationally modified finds a variety of uses. Discussion of the uses of phage displayed polypeptides is found in a variety of sources, for example, Smith and Petrenko, *Chem. Rev.*, 97:391-410 (1997).

In some embodiments, the phage-displayed polypeptide comprising an unnatural amino acid that is post-translationally modified is a member of a plurality of phage carrying the same or different encoded polypeptides, or variants of the same polypeptides (all comprising at least one unnatural amino acid). In some embodiments, where the phage display different polypeptide sequences, the displayed polypeptides comprise a library. for example, a randomized mutant library of a coding sequence of interest.

Where the phage-displayed polypeptides comprising an unnatural amino acid that is post-translationally modified constitute a library, there is generally a selection step that is applied to select the desired polypeptide species (or the nucleic acid encoding that polypeptide species) from the pool of displayed polypeptide candidates. Selection can consist of culling an initial population of phage-borne polypeptides to give a subpopulation with increased "fitness" according to some user-defined criterion. In most cases, the library input to a first round of selection is a very large initial number, and the selected subpopulation is a fraction of the initial population, where fitter clones are over represented. This population can be "amplified" by infecting fresh bacterial host cells, so that each individual phage in the subpopulation is amplified in the new amplified stock. The amplified population can then be subjected to further rounds of selection to obtain an ever-fitter subset of the starting peptides.

Generally, there are two pivotal parameters of selection, which can often be manipulated to some extent in order to enhance the efficacy of selection. First, stringency is the degree to which polypeptides with higher fitness are favored over peptides with lower fitness; second, yield is the fraction of particles with a given fitness that survive selection. The ultimate goal of selection is usually to isolate peptides with the best fitness. However, selection for the most fit polypeptides must be balanced with an appropriate stringency to allow reasonable yield. If stringency is set too high, the yield of a specifically selected phage will fall below the background of a nonspecifically isolated phage, and the power to discriminate in favor of high fitness is lost.

One of the most common selection pressures imposed on phage-displayed polypeptide populations is affinity for a target receptor. Affinity selection is ordinarily accomplished by minor modifications of standard affinity purification techniques in common use in biochemistry. Thus e.g., a receptor is tethered to a solid support, and the phage mixture is passed over the immobilized receptor. A small minority of the phage-displayed polypeptides in the library bind the receptor, and are captured on the surface or matrix, allowing unbound phages to be washed away. Finally, the bound phages are eluted in a solution that loosens the receptor-peptide interaction, yielding an "eluate" population of phages that is enriched for receptor-binding clones. The eluted phages are still infective and are propagated simply by infecting fresh bacterial host cells, yielding an "amplified" eluate that can serve as input to another round of affinity selection. Phage clones from the final eluate are propagated and characterized individually. The amino acid sequences of the peptides responsible for binding the target receptor are determined simply by ascertaining the corresponding coding sequence in the viral DNA.

Phage-borne polypeptides can be selected on the basis of fitness criteria other than affinity for a target receptor. For example, the phage carrying displayed polypeptide libraries can be selected based on a desired biological activity (e.g., an enzymatic activity, an improved enzymatic activity, or an activity that displays resistance to certain agents or repressors.).

Variations of these phage-selection schemes are numerous and are known to one of skill in the art. Furthermore, numerous publications are devoted to the subject of phage library screening methodologies.

In some embodiments, the phage displaying the polypeptide comprising the unnatural amino acid can be immobilized on a suitable support. In this aspect, the unnatural amino acid that is incorporated into the phage-displayed polypeptide can be optionally used as a reactive moiety to form a coupling with the immobilized phase, e.g., using a [3+2] cycloaddition reaction or a Staudinger ligation reaction.

The nature of the solid support to which a phage (or phage library) can be immobilized is not limited. For example, phage can be affixed to solid supports that include polystyrene dishes, impermeable plastic beads, nylon or nitrocellulose membranes, paramagnetic beads and permeable beaded agarose gels. In some embodiments, the immobilized phage are arranged in some specified relationship, i.e., they form an array. Discussion of using unnatural amino acids to form linkages with solid supports, as well as solid support formats and array can be found, for example, in International Publication WO 2004/058946, entitled "PROTEIN ARRAYS."

Orthogonal Translation System Components

In some aspects of the invention, the unnatural amino acid p-azido-L-phenylalanine (see FIG. 3, structure 2) is incorporated into a phage-displayed polypeptide of interest. When incorporated into a phage-displayed polypeptide, this unnatural amino acid can serve as chemical target for [3+2] cycloaddition reactions and in Staudinger modification reactions for posttranslational modification of the phage displayed polypeptide.

Orthogonal components for the incorporation of this unnatural amino acid are provided herein. FIG. 1 provides seven mutant *Methanococcus janaschii* tyrosyl-tRNA synthetase species (see SEQ ID NOS: 4 through 10) that charge an orthogonal suppressor tRNA with p-azido-L-phenylalanine, subsequently resulting in the incorporation of the p-azido-L-phenylalanine during translation in response to a selector codon. An orthogonal suppressor tRNA finding use with the invention is provided in SEQ ID NO: 1.

Suitable orthogonal tRNAs and aminoacyl-tRNA synthetases for the incorporation of p-azido-L-phenylalanine are also described in Chin et al., *J. Am. Chem. Soc.*, (2002) 124:9026-9027; and International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" each of which are hereby incorporated by reference in their entirety for all purposes. In addition, the prior art and present disclosure also provide guidance for the synthesis of additional orthogonal tRNAs and orthogonal aminoacyl tRNA synthetases that are not specifically recited by sequence.

In other aspects of the invention, an unnatural alkynyl amino acid, is incorporated into a phage-displayed polypeptide of interest, also to serve as a target for posttranslational modification. For example, the unnatural alkynyl amino acid para-propargyloxyphenylalanine (pPRO-Phe; see structure 9 in FIG. 15) finds use for this purpose. An alkynyl amino acid can serve as a target for [3+2] cycloaddition reactions. Orthogonal components for the incorporation of this unnatural amino acid are provided in, for example, Deiters et al, *Bioorganic & Medicinal Chemistry Letters* 15:1521-1524 (2005) and International Publication No. WO2006/034332, filed on Sep. 20, 2005.

[3+2] Cycloadditon Reaction

Unnatural amino acid side chains (e.g., on an aryl-azide amino acid or an alkynyl amino acid) can be incorporated into a phage-displayed protein of interest, then specifically and regioselectively modified by a Huisgen [3+2] cycloaddition reaction (see, Padwa, In *Comprehensive Organic Synthesis*; [Trost, B. M., Ed.] Pergamon: Oxford, 1991, Vol. 4, p 1069-1109; Huisgen, In 1,3-*Dipolar Cycloaddition Chemistry*, [Padwa, A., Ed.] Wiley: New York, 1984; p 1-176). The general reaction chemistry of the [3+2] cycloaddition reaction is shown in FIG. 15, where an azide moiety reacts with the alkynyl moiety. This reaction is irreversible and results in the formation of a triazole linkage.

As shown in FIG. 15, the R groups that are associated with either the azido or alkynyl substituents in the [3+2] cycloaddition reaction is not particularly limiting. In some aspects, the azido group forms part of an aryl-azide unnatural amino acid, for example, p-azido-L-phenylalanine, that is incorporated into a phage-displayed polypeptide (see, Example 4). In that configuration, the alkynyl moiety is attached to a reagent (e.g., the alkynyl-derivatized fluorescein dye shown in FIG. 5, structure 6 that can then be reacted with the phage displayed polypeptide, resulting in a post-translationally modified phage. The nature of the R group associated with the alkynyl group is not particularly limited.

A reverse configuration for the [3+2] cycloaddition reaction can also be employed. In this scenario, the alkynyl group is part of an alkynyl unnatural amino acid, for example, para-propargyloxyphenylalanine (see, FIG. 15, structure 9), that is incorporated into a phage-displayed polypeptide. In this configuration, the azido moiety is attached to a reagent (e.g., the azido-derivatized dansyl and fluorescein dyes shown in FIG. 16, structures 10 and 11) that can then be reacted with the phage displayed polypeptide, resulting in a post-translationally modified phage. The nature of the R group associated with the azido group is not particularly limited.

The chemistries of alkynyl and azido groups have the advantage of being completely alien to the chemistries of the endogenous functional groups present in proteins in vivo. When the [3+2] cycloaddition reaction is conducted in the presence of copper(I) at room temperature in aqueous media (conditions mild enough for modifying biological samples), it proceeds in a completely regioselective fashion (Rostovtsev et al. (2002) *Angew. Chem. Int. Ed.*, 41:2596) and can be used to selectively modify phage-displayed proteins into which alkynyl or azido functional groups have been introduced, e.g., by use of orthogonal translation system (Deiters et al. (2003) *J. Am. Chem. Soc.*, 125:11782; Wang et al. (2003) *J. Am. Chem. Soc.*, 125:3192; Link and Tirrell (2003) *J. Am. Chem. Soc.*, 125:11164). Because this method involves a cycloaddition rather than a nucleophilic substitution, proteins can be modified with extremely high selectivity. This reaction has the benefits that it can be carried out at room temperature under aqueous conditions with excellent regioselectivity (1,4>1,5) by the addition of catalytic amounts of Cu(I) salts to the reaction mixture (Tornoe et al., (2002) *J. Org. Chem.*, 67:3057-3064; Rostovtsev et al., (2002) *Angew. Chem., Int. Ed.*, 41:2596-2599).

For the purpose of demonstrating (but not limiting) the invention, the Examples herein describe the use of dansyl and fluorescein dyes that have been derivatized with either azido or alkynyl moieties and can be used in the [3+2] cycloaddition reaction. However, as it should be clear to one of skill in the art, it is not intended that the invention be limited to use of these derivatized dyes in the [3+2] cycloaddition reaction. Indeed, this chemistry permits the posttranslational modification of the phage-displayed polypeptide (and as a result, the posttranslational modification of the phage) with any molecule that can be derivatized with an azido or alkynyl moiety. It is well within the means of one of skill in the art to synthesize an azido or alkynyl derivative of any particular molecule of interest. For example, many texts and protocols are available describing how to synthesize azido compounds. For a general reference see: Patai, Saul, "The chemistry of the azido group" in *The Chemistry of Functional Groups*, London, N.Y., Interscience Publishers, 1971.

In other aspects, the invention provides compositions and methods for the generation of PEGylated phage-displayed polypeptides by using azido derivatives of polyethylene glycol (azido-PEG) for use in [3+2] cycloaddition conjugation reactions with alkynyl-containing phage-displayed polypeptides. The generalized structure of an azido polyethylene glycol is:

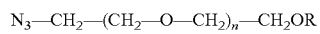

where R is H or $CH_3$, and where n is an integer between, e.g., 50 and 10,000, 75 and 5,000, 100 and 2,000, 100 and 1,000, etc. In various embodiments of the invention, the azido polyethylene glycol has a molecular weight of, e.g., about 5,000 to about 100,000 Da (i.e., about 5 kDa to about 100 kDa), about 20,000 to about 50,000 Da, about 20,000 to about 10,000 Da (e.g., 20,000 Da), etc. Techniques for the synthesis of an azido polyethylene glycol are well known to one of skill in the art. For example a polyethylene glycol molecule containing an electrophilic group (e.g., a bromide or an N-hydroxysuccinimide ester) can be reacted with a nucleophilic molecule containing an azido group (e.g., sodium azide or 3-azidopropylamine) to generate an azido polyethylene glycol.

Azido-PEG finds use with the invention when bioconjugated to an alkynyl-containing phage-displayed protein via a triazole linkage. Derivatization of protein-based therapeutics with polyethylene glycol (PEGylation) can often improve pharmacokinetic and pharmacodynamic properties of the proteins and thereby, improve efficacy and minimize dosing frequency. The various advantages of PEGylation of protein therapeutics are discussed and illustrated in, for example, Deiters et al., "Site-specific PEGylation of proteins containing unnatural amino acids," Bioorganic & Medicinal Chemistry Letters 14:5743-5745 (2004).

In addition, other advantages associated with the generation of phage-displayed polypeptides comprising unnatural alkynyl amino acids that also contain an ester linkage are contemplated. For example, a PEGylated polypeptide created by using an alkynyl amino acid with an ester linkage can allow the slow release of the polypeptide by saponification of the ester linkages in vivo or in vitro. Also, using a polymeric support (an azido resin) in place of a azido-PEG molecule enables a protein affinity purification. The triazole covalent linkage permits very strong washing steps, and the use of the ester alkynyl amino acid allows release of the phage-displayed protein by treatment with a base. Significantly, such an affinity purification scheme no longer requires the presence of an artificial tag (e.g., hexahistidine) or epitope on the protein of interest for the purification. Depending on the unnatural amino acid used, an essentially wild-type (native) polypeptide can be released from the affinity resin following the cleavage step.

Unnatural alkynyl amino acids with ester linkages can by synthesized and incorporated into proteins. See, for example, the ester linkage alkynyl amino acids in International Publication No. WO2006/034332, filed on Sep. 20, 2005. After bioconjugation via [3+2] cycloaddition, the ester linkages could be cleaved by saponification in vivo or in vitro; an application would be, e.g., the slow release of the peptide part from a PEGylated phage-displayed protein.

In other aspects, the invention provides compositions and methods for the generation of PEGylated phage-displayed polypeptides by using alkynyl derivatives of polyethylene glycol (alkynyl-PEG) for use in [3+2] cycloaddition conjugation reactions with azido-containing unnatural amino acids that are incorporated into phage-displayed polypeptides.

Staudinger Reaction

The Staudinger ligation has been previously used to selectively modify cell surface carbohydrates in both cellular and in vivo systems (Saxon and Bertozzi, Science 2000, 287, 2007-2010; Prescher et al., Nature 2004, 430, 873-877). The reaction proceeds in excellent yields under aqueous conditions and is highly selective for azide moieties. The Staudinger ligation has also been used to selectively modify proteins that contain azidohomoalanine substituted for methionine residues (Kiick et al., Proc. Natl. Acad. Sci. U.S.A. 2002, 101, 7566-7571). However, the selectivity of this Staudinger ligation approach is intrinsically limited since each methionine residue in a proteins as well as in the entire proteome are substituted with azidohomoalanine, often in competition with the native amino acid.

Figure 10:
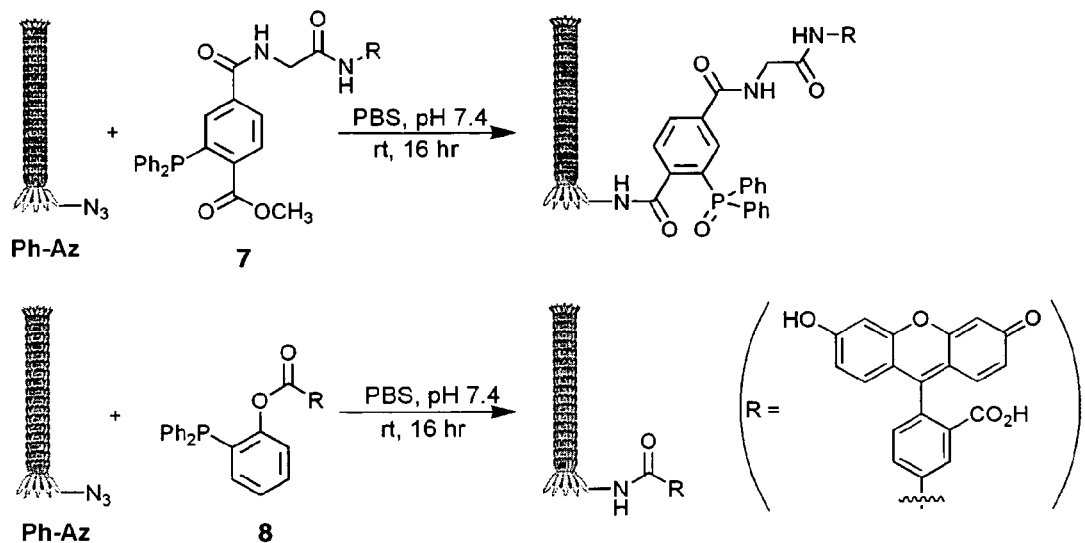
FIG. 10 shows a schematic of the Staudinger conjugation reaction involving a phage-displayed polypeptide comprising a para-azido-L-phenylalanine residue (from phage Ph-Az) with a phosphine 7 or 8.

The invention provides methods for producing a post-translationally modified phage, where the phage comprises a displayed polypeptide comprising an aryl-azide unnatural amino acid, e.g., p-azido-L-phenylalanine. That unnatural amino acid is then efficiently and specifically modified using a Staudinger ligation reaction to produce a post-translationally modified phage. FIG. 10 shows a schematic of the Staudinger ligation reaction of a phage-displayed polypeptide comprising a p-azido-L-phenylalanine residue (from phage Ph-Az) with two different spectroscopic probe phosphine molecules (structures 7 and 8). This methodology is explained in detail in Example 6.

For the purpose of demonstrating (but not limiting) the invention, the Examples herein describe the use of two spectroscopic probes that have been suitably derivatized for use in the Staudinger ligation reaction. However, as it should be clear to one of skill in the art, it is not intended that the invention be limited to use of these derivatized phosphine molecules in the Staudinger reaction. The Staudinger reaction chemistry permits the posttranslational modification of the phage-displayed polypeptide (and as a result, the posttranslational modification of the phage) with any molecule that can be suitably derivatized. It is well within the means of one of skill in the art to synthesize suitable derivatives of any particular molecule of interest for use in the conjugation.

Orthogonal tRNA/AMINOACYL-tRNA Synthetase Technology

An understanding of the novel compositions and methods of the present invention is facilitated by an understanding of the activities associated with orthogonal tRNA and orthogonal aminoacyl-tRNA synthetase pairs. Discussions of orthogonal tRNA and aminoacyl-tRNA synthetase technologies can be found, for example, in International Publications WO 2002/085923, WO 2002/086075, WO 204/09459, WO 2005/019415, WO 2005/007870 and WO 2005/007624. See also, Wang and Schultz "Expanding the Genetic Code," Angewandte Chemie Int. Ed., 44(1):34-66 (2005), the content of which is incorporated by reference in its entirety.

In order to add additional reactive unnatural amino acids to the genetic code, new orthogonal pairs comprising an aminoacyl-tRNA synthetase and a suitable tRNA are needed that can function efficiently in the host translational machinery, but that are "orthogonal" to the translation system at issue, meaning that it functions independently of the synthetases and tRNAs endogenous to the translation system. Desired characteristics of the orthologous pair include tRNA that decode or recognize only a specific codon, e.g., a selector codon, that is not decoded by any endogenous tRNA, and aminoacyl-tRNA synthetases that preferentially aminoacylate (or "charge") its cognate tRNA with only one specific unnatural amino acid. The O-tRNA is also not typically aminoacylated by endogenous synthetases. For example, in E. coli, an orthogonal pair will include an aminoacyl-tRNA synthetase that does not cross-react with any of the endogenous tRNA, e.g., which there are 40 in E. coli, and an orthogonal tRNA that is not aminoacylated by any of the endogenous synthetases, e.g., of which there are 21 in E. coli.

The invention provides phage-displayed polypeptides comprising unnatural amino acids, where the unnatural amino acid (and consequently the phage) are post-translationally modified. The incorporation of the unnatural amino acid into the phage-displayed protein is accomplished by adapting orthogonal pairs for the genetic encoding of unnatural amino acids into proteins in E. coli, where the orthogonal components do not cross-react with endogenous E. coli components of the translational machinery of the host cell, but recognize the desired unnatural amino acid and incorporate it into proteins in response to the selector codon (e.g., an amber nonsense codon, TAG). The orthogonal components provided by the invention include orthogonal aminoacyl-tRNA synthetases derived from Methanococcus jannaschii tyrosyl tRNA-synthetase, and the mutant tyrosyl tRNA$_{CUA}$ amber suppressor, which function as an orthogonal pair in a eubacterial host cell. In this system, the mutant aminoacyl-tRNA synthetases aminoacylate the suppressor tRNA with its respective unnatural amino acid and not with any of the common twenty amino acids.

This invention provides phage-displayed polypeptides comprising unnatural amino acids, where the unnatural amino acid (and consequently the phage) are post-translationally modified, and methods for producing same. These methods utilize orthogonal tRNA-aminoacyl-tRNA synthetase pairs, e.g., O-tRNA/O-RS pairs that can be used to incorporate the unnatural amino acid into the phage-displayed protein. An O-tRNA/O-RS pair is capable of mediating incorporation of an unnatural amino acid, for example, an unnatural amino acid shown in FIG. 3 or FIG. 15, into a protein that is encoded by a polynucleotide, where the polynucleotide comprises a selector codon that is recognized by the O-tRNA, e.g., in vivo. The anticodon loop of the O-tRNA recognizes the selector codon on an mRNA and incorporates its unnatural amino acid at this site in the polypeptide. Generally, an orthogonal aminoacyl-tRNA synthetase preferentially aminoacylates (or charges) its O-tRNA with only one specific unnatural amino acid.

The ability to incorporate an unnatural amino acid site-specifically into phage-displayed proteins can facilitate the study of proteins by enabling the post-translational modification of those proteins, as well as enable the engineering of proteins with novel properties. For example, expression of proteins containing one or more unnatural amino acids can facilitate the study of proteins by specific labeling, alter catalytic function of enzymes, improve biological activity or reduce cross-reactivity to a substrate, crosslink a protein with other proteins, small molecules or biomolecules, reduce or eliminate protein degradation, improve half-life of proteins in vivo (e.g., by pegylation or other modifications of introduced reactive sites), etc.

Orthogonal tRNA/Orthogonal AMINOACYL-tRNA Synthetases and Pairs Thereof

Orthogonal translation systems that are suitable for making proteins that include one or more unnatural amino acid are generally described in, for example, International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" and WO 2004/094593, entitled "EXPANDING THE EUKARYOTIC GENETIC CODE;" WO 2005/019415, filed Jul. 7, 2004; WO 2005/007870, filed Jul. 7, 2004 and WO 2005/007624, filed Jul. 7, 2004. Each of these applications is incorporated herein by reference in its entirety. See also, Wang and Schultz "Expanding the Genetic Code," *Angewandte Chemie Int. Ed.,* 44(1):34-66 (2005); Deiters et al, *Bioorganic & Medicinal Chemistry Letters* 15:1521-1524 (2005); Chin et al., *J. Am. Chem. Soc.* 2002, 124, 9026-9027; and International Publication No. WO2006/034332, filed on Sep. 20, 2005, the contents of each of which are incorporated by reference in their entirety.

Such translation systems generally comprise cells (which can be non-eukaryotic cells such as *E. coli*, or eukaryotic cells such as yeast) that include an orthogonal tRNA (O-tRNA), an orthogonal aminoacyl tRNA synthetase (O-RS), and an unnatural amino acid, where the O-RS aminoacylates the O-tRNA with the unnatural amino acid. An orthogonal pair of the invention includes an O-tRNA, e.g., a suppressor tRNA, a frameshift tRNA, or the like, and an O-RS. Individual components are also provided in the invention.

In general, when an orthogonal pair recognizes a selector codon and loads an amino acid in response to the selector codon, the orthogonal pair is said to "suppress" the selector codon. That is, a selector codon that is not recognized by the translation system's (e.g., the cell's) endogenous machinery is not ordinarily translated, which can result in blocking production of a polypeptide that would otherwise be translated from the nucleic acid. An O-tRNA of the invention recognizes a selector codon and includes at least about, e.g., a 45%, a 50%, a 60%, a 75%, a 80%, or a 90% or more suppression efficiency in the presence of a cognate synthetase in response to a selector codon as compared to the suppression efficiency of an O-tRNA comprising or encoded by a polynucleotide sequence as set forth in the sequence listing herein. The O-RS aminoacylates the O-tRNA with an unnatural amino acid of interest. The cell uses the O-tRNA/O-RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA. In certain desirable aspects, the cell can include an additional O-tRNA/O-RS pair, where the additional O-tRNA is loaded by the additional O-RS with a different unnatural amino acid. For example, one of the O-tRNAs can recognize a four base codon and the other can recognize a stop codon. Alternately, multiple different stop codons or multiple different four base codons can specifically recognize different selector codons.

In certain embodiments of the invention, a cell such as an *E. coli* cell or a yeast cell that includes an orthogonal tRNA (O-tRNA), an orthogonal aminoacyl-tRNA synthetase (O-RS), an unnatural amino acid and a nucleic acid that comprises a polynucleotide that encodes a polypeptide of interest (e.g., the phage-displayed fusion polypeptide), where the polynucleotide comprises the selector codon that is recognized by the O-tRNA. The translation system can also be a cell-free system, e.g., any of a variety of commercially available "in vitro" transcription/translation systems in combination with an O-tRNA/ORS pair and an unnatural amino acid as described herein.

In one embodiment, the suppression efficiency of the O-RS and the O-tRNA together is about, e.g., 5 fold, 10 fold, 15 fold, 20 fold, or 25 fold or more greater than the suppression efficiency of the O-tRNA lacking the O-RS. In some aspect, the suppression efficiency of the O-RS and the O-tRNA together is at least about, e.g., 35%, 40%, 45%, 50%, 60%, 75%, 80%, or 90% or more of the suppression efficiency of an orthogonal synthetase pair as set forth in the sequence listings herein.

As noted, the invention optionally includes multiple O-tRNA/O-RS pairs in a cell or other translation system, which allows incorporation of more than one unnatural amino acid into a phage-displayed polypeptide. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon), can further comprise a second orthogonal pair, where the second O-tRNA recognizes a different selector codon, e.g., an opal codon, a four-base codon, or the like. Desirably, the different orthogonal pairs are derived from different sources, which can facilitate recognition of different selector codons.

The O-tRNA and/or the O-RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases.

A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) desirably mediates incorporation of an unnatural amino acid into a protein that is encoded by a polynucleotide that comprises a selector codon that is recognized by the O-tRNA, e.g., in vivo or in vitro. In certain embodiments, an O-tRNA of the invention includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the O-tRNA sequences in the sequence listing herein.

Suppression efficiency can be determined by any of a number of assays known in the art. For example, a βgalactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Examples of O-tRNAs of the invention are set forth in the sequence listing herein. See also, the tables, examples and figures herein for sequences of exemplary O-tRNA and O-RS molecules. See also, the section entitled "Nucleic Acid and Polypeptide Sequence and Variants" herein. In an RNA molecule, such as an O-RS MRNA, or O-tRNA molecule, Thymine (T) is replace with Uracil (U) relative to a given sequence (or vice versa for a coding DNA), or complement thereof. Additional modifications to the bases can also be present.

The invention also includes conservative variations of O-tRNAs corresponding to particular O-tRNAs herein. For example, conservative variations of O-tRNA include those molecules that function like the particular O-tRNAs, e.g., as in the sequence listing herein and that maintain the tRNA L-shaped structure by virtue of appropriate self-complementarity, but that do not have a sequence identical to those, e.g., in the sequence listing, figures or examples herein (and, desirably, are other than wild type tRNA molecules). See also, the section herein entitled "Nucleic acids and Polypeptides Sequence and Variants."

The composition comprising an O-tRNA can further include an orthogonal aminoacyl-tRNA synthetase (O-RS), where the O-RS preferentially aminoacylates the O-tRNA with an unnatural amino acid. In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the cell. See also, the section herein entitled "Orthogonal aminoacyl-tRNA synthetases."

Methods of producing an orthogonal tRNA (O-tRNA) are known. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof, e.g., of the example O-tRNA of SEQ ID NO: 1.

Additional mutations can be introduced at a specific position(s), e.g., at a nonconservative position(s), or at a conservative position, at a randomized position(s), or a combination of both in a desired loop or region of a tRNA, e.g., an anticodon loop, the acceptor stem, D arm or loop, variable loop, TΦC arm or loop, other regions of the tRNA molecule, or a combination thereof. Typically, mutations in a tRNA include mutating the anticodon loop of each member of the library of mutant tRNAs to allow recognition of a selector codon. The method can further include adding additional sequences to the O-tRNA. Typically, an O-tRNA possesses an improvement of orthogonality for a desired organism compared to the starting material, e.g., the plurality of tRNA sequences, while preserving its affinity towards a desired RS.

The methods optionally include analyzing the similarity (and/or inferred homology) of sequences of tRNAs and/or aminoacyl-tRNA synthetases to determine potential candidates for an O-tRNA, O-RS and/or pairs thereof, that appear to be orthogonal for a specific organism. Computer programs known in the art and described herein can be used for the analysis, e.g., BLAST and pileup programs can be used. In one example, to choose potential orthogonal translational components for use in E. coli, a synthetase and/or a tRNA is chosen that does not display close sequence similarity to eubacterial organisms.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species.

In certain embodiments, in the negative selection, a selector codon(s) is introduced into a polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense (e.g., stop) or frameshift mutations introduced into a polynucleotide that encodes a negative selection marker, e.g., a gene for β-lactamase (bla). For example, polynucleotide variants, e.g., bla variants, with a selector codon at a certain position (e.g., A184), are constructed. Cells, e.g., bacteria, are transformed with these polynucleotides. In the case of an orthogonal tRNA, which cannot be efficiently charged by endogenous *E. coli* synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNAs or tRNAs that are not efficiently recognized by the synthetase of interest, are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation, survive both selections.

Accordingly, the same marker can be either a positive or negative marker, depending on the context in which it is screened. That is, the marker is a positive marker if it is screened for, but a negative marker if screened against.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In some aspects of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O-RS pair that loads an unnatural amino acid in response to a selector codon. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See also, Francisco et al., (1993) "Production and fluorescence-activated cell sorting of *Escherichia coli* expressing a functional antibody fragment on the external surface," *Proc Natl Acad Sci U S A.* 90:10444-8.

Additional methods for producing a recombinant orthogonal tRNA can be found, e.g., in International Application Publications WO 2002/086075, entitled "METHODS AND COMPOSITIONS FOR THE PRODUCTION OF ORTHOGONAL tRNA AMINOACYL-tRNA SYNTHETASE PAIRS;" WO 2004/094593, entitled "EXPANDING THE EUKARYOTIC GENETIC CODE;" and WO 2005/019415, filed Jul. 7, 2004. See also Forster et al., (2003) "Programming peptidomimetic synthetases by translating genetic codes designed de novo," *PNAS* 100(11):6353-6357; and, Feng et al., (2003), "Expanding tRNA recognition of a tRNA synthetase by a single amino acid change," *PNAS* 100 (10): 5676-5681.

Orthogonal aminoacyl-tRNA synthetase (O-RS)

An O-RS finding use with the invention preferentially aminoacylates an O-tRNA with an unnatural amino acid, in vitro or in vivo. An O-RS can be provided to the translation system, e.g., a cell, by a polypeptide that includes an O-RS and/or by a polynucleotide that encodes an O-RS or a portion thereof. For example, an O-RS comprises an amino acid sequence as set forth in the sequence listing and examples herein (see, e.g., FIG. 2, and SEQ ID NO: 4-7), or a conservative variation thereof. In another example, an O-RS, or a portion thereof, is encoded by a polynucleotide sequence that encodes an amino acid comprising sequence in the sequence listing or examples herein, or a complementary polynucleotide sequence thereof. See, e.g., the tables and examples herein for sequences of useful O-RS molecules. See also, the section entitled "Nucleic Acid and Polypeptide Sequence and Variants" herein.

Methods for identifying an orthogonal aminoacyl-tRNA synthetase (O-RS), e.g., an O-RS, for use with an O-tRNA, are known. For example, a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes an (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled unnatural amino acid). The active RS that more efficiently aminoacylates the second set of tRNAs compared to the first set of tRNAs is typically selected, thereby providing an efficient (optimized) orthogonal aminoacyl-tRNA synthetase for use with the O-tRNA. An O-RS, identified by the method, is also a feature of the invention.

Any of a number of assays can be used to determine aminoacylation. These assays can be performed in vitro or in vivo. For example, in vitro aminoacylation assays are described in, e.g., Hoben and Soll (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also, WO 2002/085923, entitled "IN VIVO INCORPORATION OF UNNATURAL AMINO ACIDS;" and WO 2004/094593, entitled "EXPANDING THE EUKARYOTIC GENETIC CODE."

Identified O-RS can be further manipulated to alter substrate specificity of the synthetase, so that only a desired unnatural amino acid, but not any of the common 20 amino acids, are charged to the O-tRNA. Methods to generate an orthogonal aminoacyl tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al. U.S. Pat. No. 5,756,316 to Schallenberger et al. U.S. Pat. No. 5,783,431 to Petersen et al. U.S. Pat. No. 5,824,485 to Thompson et al. U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid. In some aspects of the invention, the steps are performed multiple times, e.g., at least two times.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O-RS, and altering the substrate specificity of the synthetase can be found in Internal Publication Number WO 2002/086075, entitled "METHODS AND COMPOSITIONS FOR THE PRODUCTION OF ORTHOGONAL tRNA AMINOACYL-tRNA SYNTHETASE PAIRS;" and WO 2004/094593, entitled "EXPANDING THE EUKARYOTIC GENETIC CODE." See also, Wang and Schultz "Expanding the Genetic Code," *Angewandte Chemie Int. Ed.*, 44(1):34-66 (2005), the content of which is incorporated by reference in its entirety.

Source and Hose Organisms

The orthogonal translational components (O-tRNA and O-RS) finding use with the invention can be derived from any organism (or a combination of organisms) for use in a host translation system from any other species, with the caveat that the O-tRNA/O-RS components and the host system work in an orthogonal manner. It is not a requirement that the O-tRNA and the O-RS from an orthogonal pair be derived from the same organism. In some aspects, the orthogonal components are derived from Archaea genes (i.e., archaebacteria) for use in a eubacterial host system.

For example, the orthogonal O-tRNA can be derived from an Archae organism, e.g., an archaebacterium, such as *Methanococcus jannaschii, Methanobacterium thennoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like, or a eubacterium, such as *Escherichia coli, Thermus thermophilus, Bacillus stearothermphilus*, or the like, while the orthogonal O-RS can be derived from an organism or combination of organisms, e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus uriosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus toko-*

*daii, Thermoplasma acidophilum, Thermoplasma volcanium*, or the like, or a eubacterium, such as *Escherichia coli, Thermus thermophilus, Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms.

The O-tRNA, O-RS or O-tRNA/O-RS pair can be selected or screened in vivo or in vitro and/or used in a cell, e.g., a eubacterial cell, to produce a polypeptide with an unnatural amino acid. The eubacterial cell used is not limited, for example, *Escherichia coli, Thermus thermophilus, Bacillus stearothermphilus*, or the like. Compositions of eubacterial cells comprising translational components of the invention are also a feature of the invention.

See also, International Application Publication Number WO 2004/094593, entitled "EXPANDING THE EUKARYOTIC GENETIC CODE," filed Apr. 16, 2004, for screening O-tRNA and/or O-RS in one species for use in another species.

In some aspects, the O-tRNA, O-RS or O-tRNA/O-RS pair can be selected or screened in vivo or in vitro and/or used in a cell, e.g., a eukaryotic cell, to produce a polypeptide with an unnatural amino acid. The eukaryotic cell used is not limited; for example, any suitable yeast cell, such as *Saccharomyces cerevisiae (S. cerevisiae)* or the like, can be used. Compositions of eukaryotic cells comprising translational components of the invention are also a feature of the invention.

Although orthogonal translation systems (e.g., comprising an O-RS, an O-tRNA and an unnatural amino acid) can utilize cultured host cells to produce proteins having unnatural amino acids, it is not intended that an orthogonal translation system of the invention require an intact, viable host cell. For example, an orthogonal translation system can utilize a cell-free system in the presence of a cell extract. Indeed, the use of cell free, in vitro transcription/translation systems for protein production is a well established technique. Adaptation of these in vitro systems to produce proteins having unnatural amino acids using orthogonal translation system components described herein is well within the scope of the invention.

Selector Codons

Selector codons in orthogonal translation systems expand the genetic codon framework of protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple unnatural amino acids e.g., including at least one unnatural amino acid, using these different selector codons.

In one embodiment, the methods involve the use of a selector codon that is a stop codon for the incorporation of an unnatural amino acid in vivo in a cell into a phage-displayed polypeptide that is the target of post-translational modification. For example, an O-tRNA is produced that recognizes the stop codon and is aminoacylated by an O-RS with an unnatural amino acid. This O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers, J. R., et al., (1988), "5',3' Exonuclease in phosphorothioate-based oligonucleotide-directed mutagenesis," *Nucleic Acids Res*, 791-802. When the O-RS, O-tRNA and the nucleic acid that encodes a polypeptide of interest are combined, e.g., in vivo, the unnatural amino acid is incorporated in response to the stop codon to give a polypeptide containing the unnatural amino acid at the specified position. In one embodiment of the invention, the stop codon used as a selector codon is an amber codon, UAG, and/or an opal codon, UGA. In one example, a genetic code in which UAG and UGA are both used as a selector codon can encode 22 amino acids while preserving the ochre nonsense codon, UAA, which is the most abundant termination signal.

The incorporation of unnatural amino acids in vivo can be done without significant perturbation of the host cell. For example in non-eukaryotic cells, such as *Escherichia coli*, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present, e.g., reducing agents such as dithiothretiol (DTT).

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNA$^{Arg}$, which exists as a minor species in *Escherichia coli*. In addition, some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.*, 25:4685 (1997). Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) "Exploring the Limits of Codon and Anticodon Size," *Chemistry and Biology*, 9:237-244; and, Magliery (2001) "Expanding the Genetic Code: Selection of Efficient Suppressors of Four-base Codons and Identification of "Shifty" Four-base Codons with a Library Approach in *Escherichia coli*," *J. Mol. Biol.* 307: 755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.*, 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.*, 121:12194. In an in vivo study, Moore et al. examined the ability of tRNA$^{Leu}$ derivatives with NCUA anticodons to suppress UAGN codons (N can be U, A, G, or C), and found that the quadruplet UAGA can be decoded by a tRNA$^{Leu}$ with a UCUA anticodon with an efficiency of 13 to 26% with little decoding in the 0 or −1 frame. See Moore et al., (2000) *J. Mol. Biol.*, 298:195. In one embodiment, extended codons based on rare codons or nonsense codons can be used in invention, which can reduce missense readthrough and frameshift suppression at other unwanted sites. Four base codons have been used as selector codons in a variety of orthogonal systems. See, e.g., WO 2005/019415; WO 2005/007870 and WO 2005/07624. See also, Wang and Schultz "Expanding the Genetic Code," *Angewandte Chemie Int. Ed.*, 44(1):34-66 (2005), the content of which is incorporated by reference in its entirety. While the examples below utilize an amber selector codon, four or more base codons can be used as well, by modifying the examples herein to include four-base O-tRNAs and synthetases modified to include mutations similar to those previously described for various unnatural amino acid O-RSs.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) "An unnatural base pair for incorporating amino acid analogues into protein," *Nature Biotechnology*, 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.*, 121:11586; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See Meggers et al., (2000) *J. Am. Chem. Soc.*, 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

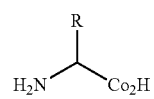

I

An unnatural amino acid is typically any structure having Formula I wherein the R group is any substituent other than one used in the twenty natural amino acids. See e.g., *Biochemistry by L. Stryer*, 3$^{rd}$ ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

Of particular interest herein are unnatural amino acids provided in FIG. 3 and FIG. 15. For example, these unnatural amino acids include but are not limited to aryl-azide amino acids, e.g., para-azido-L-phenylalanine, and alkynyl-amino acids, e.g., para-propargyloxyphenylalanine. Both the L and D-enantiomers of these unnatural amino acids find use with the invention In addition to these aryl-azide and alkynyl unnatural amino acids, other unnatural amino acids can be simultaneously incorporated into a phage-displayed polypeptide of interest, e.g., using an appropriate second O-RS/O-tRNA pair in conjunction with an orthogonal pair to incorporate the aryl-azide or alkynyl unnatural amino acid. Many such additional unnatural amino acids and suitable orthogonal pair systems are known. See the references cited herein.

In other unnatural amino acids, for example, R in Formula I optionally comprises an alkyl-, aryl-, acyl-, hydrazine, cyano-, halo-, hydrazide, alkenyl, ether, borate, boronate, phospho, phosphono, phosphine, enone, imine, ester, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety.

In another aspect, the invention provides unnatural amino acids having the general structure illustrated by Formula IV below:

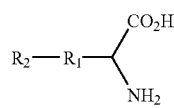

IV

An unnatural amino acid having this structure is typically any structure where $R_1$ is a substituent used in one of the twenty natural amino acids (e.g., tyrosine or phenylalanine) and $R_2$ is a substituent. Thus, this type of unnatural amino acid can be viewed as a natural amino acid derivative.

In addition to unnatural amino acids that contain novel side chains such as those shown in FIGS. 3 and 15, unnatural amino acids can also optionally comprise modified backbone structures, e.g., as illustrated by the structures of Formula II and III:

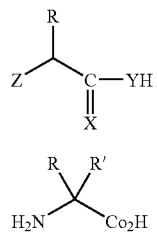

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3,4,6,7,8, and 9 membered ring proline analogues, β and γ amino acids such as substituted β-alanine and γ-amino butyric acid.

In some aspects, the invention utilizes unnatural amino acids in the L-configuration. However, it is not intended that the invention be limited to the use of L-configuration unnatural amino acids. It is contemplated that the D-enantiomers of these unnatural amino acids also find use with the invention.

Tyrosine analogs include para-substituted tyrosines, ortho-substituted tyrosines, and meta substituted tyrosines, wherein the substituted tyrosine comprises an alkynyl group, acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenylalanines, and meta-substituted phenylalanines, wherein the substituent comprises an alkynyl group, a hydroxy group, a methoxy group, a methyl group, an allyl group, an aldehyde, a nitro, a thiol group, or keto group, or the like. Specific examples of unnatural amino acids include, but are not limited to, p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenylalanine. Also, a p-propargyloxyphenylalanine, a 3,4-dihydroxy-L-phenylalanine (DHP), a 3, 4, 6-trihydroxy-L-phenylalanine, a 3,4,5-trihydroxy-L-phenylalanine, 4-nitro-phenylalanine, a p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a 3-nitro-tyrosine, a 3-thiol-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids that can be incorporated using orthogonal translation systems are known. See the references cited herein, each of which is incorporated herein by reference in its entirety.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King and Kidd, (1949) "A New Synthesis of Glutamine and of γ-Dipeptides of Glutamic Acid from Phthylated Intermediates,". *J. Chem. Soc.* 3315-3319; Friedman, and Chatterrji (1959) "Synthesis of Derivatives of Glutamine as Model Substrates for Anti-Tumor Agents," *J. Am. Chem. Soc.* 81, 3750-3752; Craig et al., (1988) "Absolute Configuration of the Enantiomers of 7-Chloro-4 [[4-(diethylamino)-1-methylbutyl]amino]quinoline (Chloroquine)," *J. Org. Chem.* 53, 1167-1170; Azoulay et al. (1991) "Glutamine analogues as Potential Antimalarials," *Eur. J. Med. Chem.* 26, 201-5; Koskinen and Rapoport (1989) "Synthesis of 4-Substituted Prolines as Conformationally Constrained Amino Acid Analogues,". *J. Org. Chem.* 54, 1859-1866; Christie and Rapoport (1985) "Synthesis of Optically Pure Pipecolates from L-Asparagine. Application to the Total Synthesis of (+)-Apovincamine through Amino Acid Decarbonylation and Iminium Ion Cyclization,". *J. Org. Chem.* 1989:1859-1866; Barton et al., (1987) "Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives," *Tetrahedron Lett.* 43:4297-4308; and, Subasinghe et al., (1992) "Quisqualic acid analogues: synthesis of beta-heterocyclic 2-aminopropanoic acid derivatives and their activity at a novel quisqualate-sensitized site," *J. Med. Chem.* 35:4602-7. See also, International Publication WO 2004/058946, entitled "PROTEIN ARRAYS," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., the toxicity assays in, e.g., International Publication WO 2004/058946, entitled "PROTEIN ARRAYS," filed on Dec. 22, 2003; and Liu and Schultz (1999) "Progress toward the evolution of an organism with an expanded genetic code," *PNAS* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), "Rapid evolution of a protein in vitro by DNA shuffling," *Nature* 370(4):389-391; and, Stemmer, (1994), "DNA shuffling by random fragmentation and reassembly: In vitro recombination for molecular evolution," *Proc. Natl. Acad. Sci. USA.*, 91:10747-10751. A related approach shuffles families of related (e.g., homologous) genes to quickly evolve enzymes with desired characteristics. An example of such "family gene shuffling" methods is found in Crameri et al., (1998) "DNA shuffling of a family of genes from diverse species accelerates directed evolution" *Nature,* 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al., (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation," *Proc. Natl. Acad. Sci. USA,* 96: 3562-67, and Ostermeier et al. (1999), "Incremental Truncation as a Strategy in the Engineering of Novel Biocatalysts," *Biological and Medicinal Chemistry,* 7:2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave and Youvan (1993) *Biotechnology Research* 11:1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "NON-STOCHASTIC GENERATION OF GENETIC VACCINES AND ENZYMES" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of *lactobacillus* for improved acid tolerance" *Nature Biotechnology*, 20(7): 707-712; and Zhang et al. (2002) "Genome shuffling leads to rapid phenotypic improvement in bacteria" Nature, Feb. 7, 415(6872): 644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.* 14(5):454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of Corynebacterium 2,5-diketo-D-gluconic acid reductase for use in vitamin C biosynthesis" *Biochemistry*, 41(20), 6226-36; Selivonova et al. (2001) "Rapid Evolution of Novel Traits in Microorganisms" *Applied and Environmental Microbiology*, 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components Finding Use with the Invention

The invention provides phage that display polypeptides comprising unnatural amino acids, where the unnatural amino acid (and consequently the phage) are post-translationally modified. The invention also provides methods for producing the modified phage.

The incorporation of the unnatural amino acid into the phage-displayed protein is accomplished by adapting orthogonal pairs for the genetic encoding of unnatural amino acids into proteins in *E. coli*, where the orthogonal components do not cross-react with endogenous *E. coli* components of the translational machinery of the host cell, but recognize the desired unnatural amino acid and incorporate it into proteins in response to the selector codon (e.g., an amber nonsense codon, TAG). The orthogonal components finding use with the invention include orthogonal aminoacyl-tRNA synthetases derived from *Methanococcus jannaschii* tyrosyl tRNA-synthetase, and the mutant tyrosyl tRNA$_{CUA}$ amber suppressor, which function as an orthogonal pair in a eubacterial host cell such as *E. coli*. In this system, the mutant aminoacyl-tRNA synthetases aminoacylate the suppressor tRNA with its respective unnatural amino acid and not with any of the common twenty amino acids.

Methods of producing orthogonal components find use with the invention, where these methods result in the incorporation of unnatural amino acids, e.g., the unnatural amino acids provided in FIG. 3 and FIG. 15, into a growing phage-displayed polypeptide chain in response to a selector codon, e.g., an amber stop codon, a nonsense codon, a four or more base codon, etc., e.g., in vivo. For example, orthogonal-tRNAs (O-tRNAs), orthogonal aminoacyl-tRNA synthetases (O-RSs) and pairs thereof find use with the invention These pairs can be used to incorporate an unnatural amino acid into growing polypeptide chains, where the polypeptide is incorporated into a phage-display system, and is subsequently post-translationally modified.

An orthogonal aminoacyl-tRNA synthetase (O-RS) finding use with the invention includes any O-RS the preferentially aminoacylates an O-tRNA with an amino acid that can be specifically and selectively post-translationally modified in a phage-display system. These amino acids include, but are not limited to, aryl-azide amino acids, e.g., para-azido-L-phenylalanine, and alkynyl-amino acids, e.g., para-propargyloxyphenylalanine. For example, the invention provides phage with a displayed polypeptide comprising at least one post-translationally modified unnatural amino acid residue, where the amino acid residue can be selectively modified. Such amino acids include but are not limited to amino acids with keto-moieties, for example, para-acetyl-L-phenylalanine, meta-acetyl-L-phenylalanine and para-(3-oxobutanoyl)-L-phenylalanine (see, e.g., Wang et al., *Proc. Natl. Acad. Sci. U.S.A.* 2003, 100:56-61 and Liu et al., (2003) JACS 125(7):1702-1703). Additional unnatural amino acids with reactive chemistries can also be incorporated into phage using orthogonal translation systems, where the unnatural amino acid is a selective target for modification. These systems can incorporate, e.g., para-(2-amino-1-hydroxyethyl)-L-phenylalanine, para-isopropylthiocarbonyl-L-phenylalanine and para-ethylthiocarbonyl-L-phenylalanine (see International Application No. PCT/US2005/039210 by Schultz et al., filed Oct. 27, 2005, entitled "ORTHOGONAL TRANSLATION COMPONENTS FOR THE IN VIVO INCORPORATION OF UNNATURAL AMINO ACIDS").

For additional information regarding unnatural amino acids that can be post-translationally modified, see, for example, the unnatural amino acid orthogonal systems described in Chin et al., *Science* (2003) 301:964-967; Zhang et al., *Proc. Natl. Acad. Sci. U.S.A.* 2004, 101:8882-8887; Anderson et al., *Proc. Natl. Acad. Sci. U.S.A.* 2004, 101:7566-7571; Wang et al., (2001) *Science* 292:498-500; Chin et al., (2002) *Journal of the American Chemical Society* 124:9026-9027; Chin and Schultz, (2002) *ChemBioChem* 11:1135-1137; Chin, et al., (2002) *PNAS United States of America* 99:11020-11024; Wang and Schultz, (2002) *Chem. Comm.*, 1-10; Wang and Schultz "Expanding the Genetic Code," *Angewandte Chemie Int. Ed.*, 44(1):34-66 (2005); Xie and Schultz, "An Expanding Genetic Code," *Methods* 36:227-238 (2005); and Deiters et al, *Bioorganic & Medicinal Chemistry Letters* 15:1521-1524 (2005), each of which is incorporated by reference in its entirety.

See also the unnatural amino acid orthogonal systems described in International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO2005/007870, filed Jul. 7, 2004; WO 2005/007624, filed Jul. 7, 2004; International Publication No. WO2006/034332, filed on Sep. 20, 2005; and International Application No. PCT/US2005/039210 by Schultz et al., filed Oct. 27, 2005, entitled "ORTHOGONAL TRANSLATION COMPONENTS FOR THE IN VIVO INCORPORATION OF UNNATURAL AMINO ACIDS."

In certain embodiments, the O-RS finding use with the invention preferentially aminoacylates the O-tRNA over any endogenous tRNA with an the particular unnatural amino acid, where the O-RS has a bias for the O-tRNA, and where the ratio of O-tRNA charged with an unnatural amino acid to the endogenous tRNA charged with the same unnatural amino acid is greater than 1:1, and more preferably where the O-RS charges the O-tRNA exclusively or nearly exclusively.

The invention also makes use of orthogonal tRNAs (O-tRNA), where the O-tRNA recognizes a selector codon. Typically, an O-tRNA includes at least about, e.g., a 45%, a 50%, a 60%, a 75%, an 80%, or a 90% or more suppression efficiency in the presence of a cognate synthetase in response to a selector codon as compared to the suppression efficiency of an O-tRNA comprising or encoded by a polynucleotide sequence as set forth in the sequence listings (e.g., SEQ ID NO: 1). In one embodiment, the suppression efficiency of the O-RS and the O-tRNA together is, e.g., 5 fold, 10 fold, 15 fold, 20 fold, 25 fold or more greater than the suppression efficiency of the O-tRNA in the absence of an O-RS. In some aspects, the suppression efficiency of the O-RS and the O-tRNA together is at least 45% of the suppression efficiency of an orthogonal tyrosyl-tRNA synthetase pair derived from *Methanococcus jannaschii*.

The invention makes use of cells (e.g., *E. coli*) comprising a translation system and nucleotide sequences that program phage production, where the translation system includes an orthogonal-tRNA (O-tRNA), an orthogonal aminoacyl-tRNA synthetase (O-RS), and, an unnatural amino acid that can be post-translationally modified following its incorporation into the phage-displayed polypeptide. Typically, the O-RS preferentially aminoacylates the O-tRNA over any endogenous tRNA with the unnatural amino acid, where the O-RS has a bias for the O-tRNA, and where the ratio of O-tRNA charged with the unnatural amino acid to the endogenous tRNA charged with the unnatural amino acid is greater than 1:1, and more preferably where the O-RS charges the O-tRNA exclusively or nearly exclusively. The O-tRNA recognizes the first selector codon, and the O-RS preferentially aminoacylates the O-tRNA with an unnatural amino acid.

Various polynucleotides also find use with the invention. These polynucleotides include an artificial (e.g., man-made, and not naturally occurring, e.g., recombinant) polynucleotide comprising a nucleotide sequence encoding an O-RS. A polynucleotide finding use with the invention can also includes a nucleic acid that hybridizes to a polynucleotide described above, under highly stringent conditions, over substantially the entire length of the nucleic acid. Vectors comprising polynucleotides also find use with the invention. For example, a vector can include a plasmid, a cosmid, a phage, a virus, an expression vector, and/or the like. Methods for producing components of an O-tRNA/O-RS pair are known and find use with the invention. See the present disclosure and the reference cited herein.

Nucleic Acid and Polypeptide Sequence and Variants

As described herein, polynucleotide sequences encoding, e.g., O-tRNAs and O-RSs, find use with the invention, as do the respective amino acid sequences encoded by the polynucleotides. The disclosure provides and references examples of polynucleotide and polypeptide sequences that find use with the invention. However, it will be appreciated that use of the invention is not limited to those sequences disclosed herein. One of skill will appreciate that the invention also provides many related sequences with the functions described herein, e.g., polynucleotides and polypeptides encoding conservative variants of an O-RS disclosed herein.

A polynucleotide finding use with the invention also includes an artificial polynucleotide that is, e.g., at least 75%, at least 80%, at least 90%, at least 95%, at least 98% or more identical to that of a naturally occurring tRNA, (but is other than a naturally occurring tRNA). A polynucleotide finding use with the invention also includes an artificial polynucleotide that is, e.g., at least 75%, at least 80%, at least 90%, at least 95%, at least 98% or more identical (but not 100% identical) to that of a naturally occurring tRNA.

In certain embodiments, a vector finding use with the invention (e.g., a plasmid, a cosmid, a phage, a virus, etc.) comprises a polynucleotide that finds use with the invention. In some embodiments, the vector is an expression vector. In other embodiments, the expression vector includes a promoter operably linked to one or more of the polynucleotides of the invention. In other embodiments, a cell comprises a vector that includes a polynucleotide finding use with the invention.

One of skill will appreciate that many variants of the disclosed sequences also find use with the invention. For example, conservative variations of the disclosed sequences that yield a functionally identical sequence find use with the invention. Variants of the nucleic acid polynucleotide sequences, wherein the variants hybridize to at least one disclosed sequence, find use with the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE 1

Conservative Amino Acid Substitutions

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids that find use with the invention, including conservative variations of nucleic acids provided herein, and this comparative hybridization method is a preferred method of distinguishing nucleic acids that find use with the invention. Target nucleic acids which hybridize to nucleic acids provided or referenced herein under high, ultra-high and ultra-ultra high stringency conditions also find use with the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes*, Part I, Chapter 2, "Overview of principles of hybridization and the strategy of nucleic acid probe assays," (Elsevier, New York), as well as in *Current Protocols in Molecular Biology*, Ausubel et al., eds., Current Protocols, a joint venture between Greene Publishing Associates, Inc. and John Wiley & Sons, Inc., (supplemented through 2004) ("Ausubel"); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention utilizes a nucleic acid that comprises a unique subsequence in a nucleic acid selected from the sequences of O-tRNAs and O-RSs disclosed or referenced herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention.

Similarly, the invention utilizes a polypeptide which comprises a unique subsequence in a polypeptide selected from the sequences of O-RSs disclosed or referenced herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, *Guide to Molecular Cloning Techniques Methods in Enzymology volume* 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2004) ("Ausubel"). These texts describe mutagenesis, the use of vectors, promoters and many other relevant topics related to, e.g., the generation of genes that include selector codons for production of proteins that include unnatural amino acids, orthogonal tRNAs, orthogonal synthetases, and pairs thereof.

Various types of mutagenesis can be used in conjunction with the invention, e.g., to mutate tRNA molecules, to produce libraries of tRNAs, to produce libraries of synthetases, to insert selector codons that encode an unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide, e.g., a vector, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman and Smith, *Gene* 8:81 (1979); Roberts, et al., *Nature* 328:731 (1987); Schneider, B., et al., *Protein Expr. Purif.* 6435:10 (1995); Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)), and/or the like.

A highly efficient and versatile single plasmid system was developed for site-specific incorporation of unnatural amino acids into proteins in response to the amber stop codon (UAG) in *E. coli*. In the new system, the pair of *M. jannaschii* suppressor tRNAtyr(CUA) and tyrosyl-tRNA synthetase are encoded in a single plasmid, which is compatible with most *E. coli* expression vectors. Monocistronic tRNA operon under control of proK promoter and terminator was constructed for optimal secondary structure and tRNA processing. Introduction of a mutated form of glnS promoter for the synthetase resulted in a significant increase in both suppression efficiency and fidelity. Increases in suppression efficiency were also obtained by multiple copies of tRNA gene as well as by a specific mutation (D286R) on the synthetase (Kobayashi et al., "Structural basis for orthogonal tRNA specificities of tyrosyl-tRNA synthetases for genetic code expansion," Nat. Struct. Biol., 10(6):425-432 [2003]). The generality of the optimized system was also demonstrated by highly efficient and accurate incorporation of several different unnatural amino acids, whose unique utilities in studying protein function and structure were previously proven.

A catalogue of Bacteria and Bacteriophages useful for cloning is provided, e.g., by the ATCC, e.g., *The ATCC Catalogue of Bacteria and Bacteriophae* (1996) Gherna et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition* Scientific American Books, NY. In addition, essentially any nucleic acid (and virtually any labeled nucleic acid, whether standard or nonstandard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells. a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

Methods of producing a phage with a displayed fusion protein comprising an unnatural amino acid (an aryl-azide amino acid or an alkynyl-amino acid) at a specified position that is post-translationally modified are also a feature of the invention. For example, a method can include growing, in an appropriate medium, the cell with the phage construct (e.g., in an *E. coli* cell), where the cell comprises a nucleic acid that comprises at least one selector codon and encodes a protein (the capsid fusion protein); and, providing the unnatural amino acid; where the cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the unnatural amino acid. The phage so produced in the *E. coli* comprises a displayed fusion protein having an unnatural amino acid at the position corresponding to the selector codon. That phage is then reacted under conditions where the unnatural amino acid undergoes covalent modification, thereby producing a post-translationally modified phage.

In certain embodiments, the O-RS comprises a bias for the aminoacylation of the cognate O-tRNA over any endogenous tRNA in an expression system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

In some embodiments, the phage-displayed, post-translationally modified fusion proteins can be cleaved using a suitable protease and a protease recognition sequence that has been incorporated into the phage-displayed fusion protein. This cleavage can result in the release of the protein of interest, or a portion thereof, from the phage capsid. In some embodiments, the protein of interest comprises an amino acid sequence that is at least 75% identical to that of a therapeutic protein, a diagnostic protein, an industrial enzyme, or portion thereof.

The phage with a displayed fusion protein comprising an unnatural amino acid (e.g., an aryl-azide amino acid or an alkynyl-amino acid) at a specified position that is post-translationally modified is a feature of the invention. The phage is produced in a cell, e.g., an *E. coli* cell. The O-tRNA/O-RS pairs also reside in the cell and utilize the host cell's translation machinery, which results in the in vivo incorporation of an unnatural amino acid into a fusion protein in response to a selector codon and displayed on the phage. The ability of an O-tRNA/O-RS system to function in a host cell to incorporate a wide variety of unnatural amino acids that can be post-translationally modified is known. See, e.g., Chin et al., *Science* (2003) 301:964-967; Zhang et al., *Proc. Natl. Acad. Sci. U.S.A.* 2004, 101:8882-8887; Anderson et al., *Proc. Natl. Acad. Sci. U.S.A.* 2004, 101:7566-7571; Wang et al., (2001) *Science* 292:498-500; Chin et al., (2002) *Journal of the American Chemical Society* 124:9026-9027; Chin and Schultz, (2002) *ChemBioChem* 11:1135-1137; Chin, et al., (2002) *PNAS United States of America* 99:11020-11024; Wang and Schultz, (2002) *Chem. Comm.*, 1-10; Wang and Schultz "Expanding the Genetic Code," *Angewandte Chemie Int*. Ed., 44(1):34-66 (2005); xie and Schultz, "An Expanding Genetic Code," *Methods* 36:227-238 (2005); and Deiters et al, *Bioorganic & Medicinal Chemistry Letters* 15:1521-1524 (2005), each of which is incorporated by reference in its entirety.

See also the unnatural amino acid orthogonal systems described in International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO2005/007870, filed Jul. 7, 2004; WO 2005/007624, filed Jul. 7, 2004; International Publication No. WO2006/034332, filed on Sep. 20, 2005; and International Application No. PCT/US2005/039210 by Schultz et al., filed Oct. 27, 2005, entitled "ORTHOGONAL TRANSLATION COMPONENTS FOR THE IN VIVO INCORPORATION OF UNNATURAL AMINO ACIDS," each of which is incorporated by reference in its entirety.

The incorporation of an unnatural amino acid can be done to, e.g., tailor changes in protein structure and/or function, e.g., to change size, acidity, nucleophilicity, hydrogen bonding, hydrophobicity, accessibility of protease target sites, target to a moiety (e.g., for a protein array), incorporation of labels or reactive groups, etc. Proteins that include an unnatural amino acid can have enhanced or even entirely new catalytic or physical properties. For example, the following properties are optionally modified by inclusion of an unnatural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid are useful for, e.g., novel therapeutics, diagnostics, catalytic enzymes, industrial enzymes, binding proteins (e.g., antibodies), and e.g., the study of protein structure and function. See, e.g., Dougherty, (2000) "Unnatural Amino Acids as Probes of Protein Structure and Function," *Current Opinion in Chemical Biology*, 4:645-652. Proteins that comprise an unnatural amino acid that can be selectively post-translationally modified (e.g., by a [3+2] cycloaddition or a Staudinger modification) can be engineered to contain any desired functionality that can be coupled to the reaction partner. The nature of the reaction partner is not limited in any way, except only that it comprise a suitable reactive moiety that results in a covalent attachment to the unnatural amino acid residue in the phage-displayed polypeptide.

In some aspects, a composition includes at least one phage-displayed protein with at least one, e.g., at least two, at least three, at least four, at least five, at least six, at least seven, at least eight, at least nine, or at least ten or more unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a phage-displayed protein with at least one, but fewer than all, of a particular amino acid present in the protein is an unnatural amino acid. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any phage-displayed protein (or portion thereof) that includes an unnatural amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more unnatural amino acid can be found, but not limited to, those in International Publications WO 2004/094593, filed Apr. 16, 2004, entitled "Expanding the Eukaryotic Genetic Code;" and, WO 2002/085923, entitled "IN VIVO INCORPORATION OF UNNATURAL AMINO ACIDS." Examples of therapeutic, diagnostic, and other proteins that can be modified to comprise one or more unnatural amino acids include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-i alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-s, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation and modification of unnatural amino acids into phage-displayed proteins described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more unnatural amino acids) include biologically active proteins such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40/CD40, VLA-4VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one unnatural amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma BioSciences catalogue), and the corresponding protein sequences and genes and, typically, many variants thereof, are well-known (see, e.g., Genbank). Any of them can be modified by the insertion of one or more unnatural amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more unnatural amino acid using compositions and methods of the invention. For example, the invention can include substituting one or more natural amino acids in one or more vaccine proteins with an unnatural amino acid, e.g., in proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., *vaccinia*; Picornaviruses, e.g. *polio*; Togaviruses, e.g., *rubella*; Flaviviruses, e.g., HCV; and Coronaviruses), (–) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for unnatural amino acid modification.

In certain embodiments, the modified phage-displayed protein of interest (or portion thereof) is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of an unnatural amino acid. For example, a nucleic acid for a protein of interest is mutagenized to include one or more selector codon, providing for the insertion of the one or more unnatural amino acids. The invention includes any such variant, e.g., mutant, versions of any protein, e.g., including at least one unnatural amino acid. Similarly, the invention also includes corresponding nucleic acids, i.e., any nucleic acid with one or more selector codon that encodes one or more unnatural amino acid.

To make a phage-displayed protein that includes a post-translationally modified unnatural amino acid, one can use host cells and organisms that are adapted for the in vivo incorporation of the unnatural amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., polypeptides comprising unnatural amino acids in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional details on proteins, antibodies, antisera, etc. can be found in International Publication Numbers WO 2004/094593, entitled "EXPANDING THE EUKARYOTIC GENETIC CODE;" WO 2002/085923, entitled "IN VIVO INCORPORATION OF UNNATURAL AMINO ACIDS;" WO 2004/035605, entitled "GLYCOPROTEIN SYNTHESIS;" and WO 2004/058946, entitled "PROTEIN ARRAYS."

Photoregulation and Photocaging

The invention provides phage having displayed polypeptides comprising at least one unnatural amino acid that is post-translationally modified. The-posttranslational modification can result in the attachment of any desired moiety onto the capsid fusion polypeptide (and consequently onto the phage). In some embodiments, the conjugated moiety that is coupled to the unnatural amino acid is photoregulated, thereby producing a photoregulated modified unnatural amino acid.

Photoregulated amino acids (e.g., photochromic, photocleavable, photoisomerizable, etc.) can be used to spatially and temporally control a variety of biological process, e.g., by directly regulating the activity of enzymes, receptors, ion channels or the like, or by modulating the intracellular concentrations of various signaling molecules. See, e.g., Shigeri et al., *Pharmacol. Therapeut.*, 2001, 91:85; Curley, et al., *Pharmacol. Therapeut.*, 1999, 82:347; Curley, et al., *Curr. Op. Chem. Bio.*, 1999, 3:84; "Caged Compounds" *Methods in Enzymology*, Marriott, G., Ed, Academic Press, NY, 1998, V. 291; Adams, et al., *Annu. Rev. Physiol.*, 1993, 55:755+; and Bochet, et al., *J. Chem. Soc., Perkin* 1, 2002, 125. In various embodiments herein, the compositions and methods comprise photoregulated amino acids.

"Photoregulated amino acids" are typically, e.g., photosensitive amino acids. Photoregulated amino acids in general are those that are controlled in some fashion by light (e.g., UV, IR, etc.). Thus, for example, if a photoregulated amino acid is incorporated into a polypeptide having biological activity, illumination can alter the amino acid, thereby changing the biological activity of the peptide. Some photoregulated amino acids can comprise "photocaged amino acids," "photosensitive amino acids," "photolabile amino acids," "photoisomerizable," etc. "Caged species," such as caged amino acids, or caged peptides, are those trapped inside a larger entity (e.g., molecule) and that are released upon specific illumination. See, e.g., Adams, et al., Annu. Rev. Physiol., 1993, 55:755-784. "Caging" groups of amino acids can inhibit or conceal (e.g., by disrupting bonds which would usually stabilize interactions with target molecules, by changing the hydrophobicity or ionic character of a particular side chain, or by steric hindrance, etc.) biological activity in a molecule, e.g., a peptide comprising such amino acid. "Photoisomerizable" amino acids can switch isomer forms due to light exposure. The different isomers of such amino acids can end up having different interactions with other side chains in a protein upon incorporation. Photoregulated amino acids can thus control the biological activity (either through activation, partial activation, inactivation, partial inactivation, modified activation, etc.) of the peptides in which they are present. See Adams above and other references in this section for further definitions and examples of photoregulated amino acids and molecules.

A number of photoregulated amino acids are known to those in the art and many are available commercially. Methods of attaching and/or associating photoregulating moieties to amino acids are also known. Such photoregulated amino acids in general are amenable to various embodiments herein. It will be appreciated that while a number of possible photoregulating moieties, e.g., photocaging groups and the like, as well as a number of photoregulated amino acids are listed herein, such recitation should not be taken as limiting. Thus, the current invention is also amenable to photoregulating moieties and photoregulated amino acids that are not specifically recited herein.

As stated, a number of methods are optionally applicable to create a photoregulated amino acid. Thus, for example, a photoregulated amino acid, e.g., a photocaged amino acid can be created by protecting its α-amino group with compounds such as BOC (butyloxycarbonyl), and protecting the α-carboxyl group with compounds such as a t-butyl ester. Such protection can be followed by reaction of the amino acid side chain with a photolabile caging group such as 2-nitrobenzyl, in a reactive form such as 2-nitrobenzylchloroformate, α-carboxyl 2-nitrobenzyl bromide methyl ester, or 2-nitrobenzyl diazoethane. After the photolabile cage group is added, the protecting groups can be removed via standard procedures. See, e.g., U.S. Pat. No. 5,998,580.

As another example, lysine residues can be caged using 2-nitrobenzylchloroformate to derivatize the ε-lysine amino group, thus eliminating the positive charge. Alternatively, lysine can be caged by introducing a negative charge into a peptide (which has such lysine) by use of an α-carboxy 2-nitrobenzyloxycarbonyl caging group. Additionally, phosphoserine and phosphothreonine can be caged by treatment of the phosphoamino acid or the phosphopeptide with 1(2-nitrophenyl)diazoethane. See, e.g., Walker et al., *Meth Enzymol.* 172: 288-301, 1989. A number of other amino acids are also easily amenable to standard caging chemistry, for example serine, threonine, histidine, glutamine, asparagine, aspartic acid and glutamic acid. See, e.g., Wilcox et al., *J. Org. Chem.* 55:1585-1589, 1990). Again, it will be appreciated that recitation of particular photoregulated (amino acids and/or those capable of being converted to photoregulated forms) should not necessarily be taken as limiting.

Amino acid residues can also be made photoregulated (e.g., photosensitive or photolabile) in other fashions. For example, certain amino acid residues can be created wherein irradiation causes cleavage of a peptide backbone that has the particular amino acid residue. For example a photolabile glycine, 2-nitrophenyl glycine, can function in such a manner. See, e.g., Davis, et al., 1973, *J. Med. Chem.*, 16:1043-1045. Irradiation of peptides containing 2-nitrophenylglycine will cleave the peptide backbone between the alpha carbon and the alpha amino group of 2-nitrophenylglycine. Such cleavage strategy is generally applicable to amino acids other than glycine, if the 2-nitrobenzyl group is inserted between the alpha carbon and the alpha amino group.

A large number of photoregulating groups, e.g., caging groups, and a number of reactive compounds used to covalently attach such groups to other molecules such as amino acids, are well known in the art. Examples of photoregulating (e.g., photolabile, caging) groups include, but are not limited to: o-nitrobenzyl-serine, O-(2-nitrobenzyl)-L-tyrosine, nitroindolines; N-acyl-7-nitroindolines; phenacyls; hydroxyphenacyl; brominated 7-hydroxycoumarin-4-ylmethyls (e.g., Bhc); benzoin esters; dimethoxybenzoin; meta-phenols; 2-nitrobenzyl; 1-(4,5-dimethoxy-2-nitrophenyl) ethyl (DMNPE); 4,5-dimethoxy-2-nitrobenzyl (DMNB); alpha-carboxy-2-nitrobenzyl (CNB); 1-(2-nitrophenyl)ethyl (NPE); 5-carboxymethoxy-2-nitrobenzyl (CMNB); (5-carboxymethoxy-2-nitrobenzyl)oxy) carbonyl; (4,5-dimethoxy-2-nitrobenzyl)oxy) carbonyl; desoxybenzoinyl; and the like. See, e.g., U.S. Pat. No. 5,635,608 to Haugland and Gee (Jun. 3, 1997) entitled "α-carboxy caged compounds" *Neuro* 19, 465 (1997); *J Physiol* 508.3, 801 (1998); *Proc Natl Acad Sci USA* 1988 September, 85(17):6571-5; *J Biol Chem* 1997 Feb. 14, 272(7):4172-8; *Neuron* 20, 619-624, 1998; *Nature Genetics*, vol. 28:2001:317-325; *Nature*, vol. 392, 1998:936-941; Pan, P., and Bayley, H. "Caged cysteine and thiophosphoryl peptides" *FEBS Letters* 405:81-85 (1997); Pettit et al. (1997) "Chemical two-photon uncaging: a novel approach to mapping glutamate receptors" *Neuron* 19:465-471; Furuta et al. (1999) "Brominated 7-hydroxycoumarin-4-ylmethyls: novel photolabile protecting groups with biologically useful cross-sections for two photon photolysis" *Proc. Natl. Acad. Sci.* 96(4): 1193-1200; Zou et al. "Catalytic subunit of protein kinase A caged at the activating phosphothreonine" *J. Amer. Chem. Soc.* (2002) 124:8220-8229; Zou et al. "Caged Thiophosphotyrosine Peptides" *Angew. Chem. Int. Ed.* (2001) 40:3049-3051; Conrad II et al. "p-Hydroxyphenacyl Phototriggers: The reactive Excited State of Phosphate Photorelease" *J. Am. Chem. Soc.* (2000) 122:9346-9347; Conrad II et al. "New Phototriggers 10: Extending the π,π* Absorption to Release Peptides in Biological Media" *Org. Lett.* (2000) 2:1545-1547; Givens et al. "A New Phototriggers 9: p-Hydroxyphenacyl as a C-Terminus Photoremovable Protecting Group for Oligopeptides" *J. Am. Chem. Soc.* (2000) 122: 2687-2697; Bishop et al. "40-Aminomethyl-2,20-bipyridyl-4-carboxylic Acid (Abc) and Related Derivatives: Novel Bipyridine Amino Acids for the Solid-Phase Incorporation of a Metal Coordination Site Within a Peptide Backbone" *Tetrahedron* (2000) 56:4629-4638; Ching et al. "Polymers As Surface-Based Tethers with Photolytic triggers Enabling Laser-Induced Release/Desorption of Covalently Bound Molecules" *Bioconjugate Chemistry* (1996) 7:525-8; Bio-Probes Handbook, 2002 from Molecular Probes, Inc.; and *Handbook of Fluorescent Probes and Research Products*, Ninth Edition or Web Edition, from Molecular Probes, Inc, as well as the references herein. Many compounds, kits, etc. for use in caging various molecules are commercially available, e.g., from Molecular Probes, Inc. Additional references are found in, e.g., Merrifield, Science 232:341 (1986) and Corrie, J. E. T. and Trentham, D. R. (1993) In: Biological Applications of Photochemical Switches, ed., Morrison, H., John Wiley and Sons, Inc. New York, pp. 243-305. Examples of suitable photosensitive caging groups include, but are not limited to, 2-nitrobenzyl, benzoin esters, N-acyl-7-nitindolines, meta-phenols, and phenacyls.

In some embodiments, a photoregulating (e.g., caging) group can optionally comprise a first binding moiety, which can bind to a second binding moiety. For example, a commercially available caged phosphoramidite [1-N-(4,4'-Dimethoxytrityl)-5-(6-biotinamidocaproamidomethyl)-1-(2-nitrophenyl)-ethyl]-2-cyanoethyl-(N,N-diisopropyl)-phosphoramidite (PC Biotin Phosphoramadite, from Glen Research Corp.) comprises a photolabile group and a biotin (the first binding moiety). A second binding moiety, e.g., streptavidin or avidin, can thus be bound to the caging group, increasing its bulkiness and its effectiveness at caging. In certain embodiments, a caged component comprises two or more caging groups each comprising a first binding moiety, and the second binding moiety can bind two or more first binding moieties simultaneously. For example, the caged component can comprise at least two biotinylated caging groups; binding of streptavidin to multiple biotin moieties on multiple caged component molecules links the caged components into a large network. Cleavage of the photolabile group attaching the biotin to the component results in dissociation of the network.

Traditional methods of creating caged polypeptides (including e.g. peptide substrates and proteins such as antibodies or transcription factors) include, e.g., by reacting a polypeptide with a caging compound or by incorporating a caged amino acid during synthesis of a polypeptide. See, e.g., U.S. Pat. No. 5,998,580 to Fay et al. (Dec. 7, 1999) entitled "Photosensitive caged macromolecules"; Kossel et al. (2001) *PNAS* 98:14702-14707; *Trends Plant Sci* (1999) 4:330-334; *PNAS* (1998) 95:1568-1573; *J. Am. Chem. Soc.* (2002) 124: 8220-8229; *Pharmacology & Therapeutics* (2001) 91:85-92; and *Angew. Chem. Int. Ed. Engl.* (2001) 40:3049-3051. A photolabile polypeptide linker (e.g., for connecting a protein transduction domain and a sensor, or the like) can, for example, comprise a photolabile amino acid such as that described in U.S. Pat. No. 5,998,580.

Irradiation with light can, e.g., release a side chain residue of an amino acid that is important for activity of the peptide comprising such amino acid. Additionally, in some embodiments, uncaged amino acids can cleave the peptide backbone of the peptide comprising the amino acid and can thus, e.g., open a cyclic peptide to a linear peptide with different biological properties, etc.

Activation of a caged peptide can be done through destruction of a photosensitive caging group on a photoregulated amino acid by any standard method known to those skilled in the art. For example, a photosensitive amino acid can be uncaged or activated by exposure to a suitable conventional light source, such as lasers (e.g., emitting in the UV range or infrared range). Those of skill in the art will be aware of and familiar with a number of additional lasers of appropriate wavelengths and energies as well as appropriate application protocols (e.g., exposure duration, etc.) that are applicable to use with photoregulated amino acids such as those utilized herein. Release of photoregulated caged amino acids allows control of the peptides that comprise such amino acids. Such control can be both in terms of location and in terms of time. For example, focused laser exposure can uncage amino acids in one location, while not uncaging amino acids in other locations.

Those skilled in the art will appreciate a variety of assays can be used for evaluating the activity of a photoregulated amino acid, e.g., the assays described in the examples herein. A wide range of, e.g., cellular function, tissue function, etc. can be assayed before and after the introduction of a peptide comprising a photoregulated amino acid into the cell or tissue as well as after the release of the photoregulated molecule.

The compositions and methods herein can be utilized in a number of aspects. For example, photoregulated amino acids (e.g., in peptides) can deliver therapeutic compositions to discrete locations of a body since the release or activation/deactivation/etc. of the photoregulated amino acid can be localized through targeted light exposure, etc. It will also be appreciated that the methods, structures, and compositions of the invention are applicable to incorporation/use of photoregulated natural amino acids (e.g., ones with photoregulating moieties attached/associated with them).

Photochromic and photocleavable groups can be used to spatially and temporally control a variety of biological processes, either by directly regulating the activity of enzymes (see, e.g., Westmark, et al., *J. Am. Chem. Soc.* 1993, 115: 3416-19 and Hohsaka, et al., *J. Am. Chem. Soc.* 1994, 116: 413-4), receptors (see, e.g., Bartels, et al., *Proc. Natl. Acad. Sci. USA,* 1971, 68:1820-3; Lester, et al., *Nature* 1977, 266: 373-4: Cruz, et al., *J. Am. Chem. Soc.,* 2000, 122:8777-8; and, Pollitt, et al., *Angew. Chem. Int. Ed. Engl.,* 1998, 37:2104-7), or ion channels (see, e.g., Lien, et al., *J. Am. Chem. Soc.* 1996, 118:12222-3; Borisenko, et al., *J. Am. Chem. Soc.* 2000, 122:6364-70; and, Banghart, et al., *Nat. Neurosci.* 2004, 7:1381-6.), or by modulating the intracellular concentrations of various signaling molecules (see, e.g., Adams, et al., *Annu. Rev. Physiol.* 1993, 55:755-84). In general, this requires the chemical modification of either a protein or small molecule with a photoreactive ligand such as azobenzene or a nitrobenzyl group. The ability to genetically incorporate photoresponsive amino acids into proteins at defined sites directly in living organisms would significantly extend the scope of this technique. See, e.g., Wu, et al., *J. Am. Chem. Soc.* 2004, 126: 14306-7.

Kits

Kits are also a feature of the invention. For example, a kit for producing a phage having a displayed polypeptide comprising at least one unnatural amino acid that is post-translationally modified is a feature of the invention. For example, such kits can comprise various components selected from: a container to hold the kit components, instructional materials for producing the modified phage, a nucleic acid comprising the phage genomic material, nucleic acid comprising a polynucleotide sequence encoding an O-tRNA, nucleic acid comprising a polynucleotide encoding an O-RS, an unnatural amino acid, for example an aryl-azide amino acid (e.g., para-azido-L-phenylalanine) or an alkynyl-amino acid (e.g., para-propargyloxyphenylalanine), reagents for the post-translational modification of the unnatural amino acid (e.g., reagents for the Staudinger ligation or the [3+2] cycloaddition reaction), and a suitable strain of E. coli host cells for expression of the O-tRNA/O-RS and production of the phage.

EXAMPLES

The following examples are offered to illustrate, but not to limit the claimed invention. One of skill will recognize a variety of non-critical parameters that may be altered without departing from the scope of the claimed invention.

Example 1

The Generation of Phage Displayed Polypeptides Comprising Unnatural Amino Acids

The present Example describes compositions and methods for the generation of phage displayed polypeptides comprising unnatural amino acids. As described previously, orthogonal translation components can be used in suitable host cells to selectively introduce any of a large number of unnatural amino acids into proteins in vivo with good efficiency and high fidelity. As described herein, these orthogonal translation components and methodologies can be adapted for use in phage display systems as a general approach to the generation of phage-displayed polypeptide libraries containing unnatural amino acid building blocks.

Two plasmids, pDULE/CM and M13KE, were used to generate phage that display polypeptides containing unnatural amino acids as fusions to the pIII protein of the M13 filamentous phage. Plasmid pDULE/CM, which has a p15A origin, constitutively expresses a Methanococcus jannaschii amber suppressor tRNATyr (MjtRNA) and a mutant M. jannaschii tyrosyl-tRNA synthetase (MjTyrRS; synthetase variant clone number 7 as described in Chin et al., J. Am. Chem. Soc., (2002) 124:9026-9027; see also FIG. 2 and SEQ ID NO: 10) in Escherichia coli. This mutant MjTyrRS aminoacylates the amber suppressor tRNA (e.g., the orthogonal tRNA shown in FIG. 1; SEQ ID NO: 1) with the desired unnatural amino acid (e.g., the amino acids shown in FIG. 3). Growth of E. coli Top 10 F' harboring pDULE/CM (designated strain TTS) in the presence of the corresponding unnatural amino acid results in the incorporation of the unnatural amino acid at the site specified by the amber codon TAG. The second plasmid, M13KE, was a phage vector used for pentavalent N-terminal pIII display; a derivative, pM13KE-SBP, displaying a pIII fusion streptavidin binding peptide (SBP), AGXTL-LAHPQ (SEQ ID NO: 11), was used in this study. The N-terminal AG sequence facilitates cleavage of the signal peptide. The third residue, X, encoded by amber nonsense codon TAG, designates the unnatural amino acid to be incorporated. Expression of the pIII fusion protein in E. coli strain TTS in the presence of the unnatural amino acid should afford viable phage that display the peptide containing the unnatural amino acid as a pIII fusion. To prepare the initial phage stocks, plasmid pM13KE-SBP was transformed into the E. coli strain XL1-Blue, a natural amber suppression strain that incorporates glutamine at residue X.

To examine the dependence of phage plaque formation on the presence of the unnatural amino acid, M13KE-SBP phage and M13KE wild-type phages were plated on E. coli strain TTS/RS 3 cell lawns (where RS 3 designates an aminoacyl tRNA synthetase specific for p-acetylphenylalanine, structure 3 in FIG. 3) in the presence and absence of 2 mM p-acetylphenylalanine 3. In the presence of the unnatural amino acid, both M13KE-SBP phage and M13KE wild-type phage formed normal-sized plaques after overnight incubation at 37° C. However, in the absence of the unnatural amino acid, only M13KE wild-type phage formed plaques. No plaque formation was observable for M13KE-SBP phage in the absence of p-acetyl-phenylalanine. The M13KE-SBP phage yield in the natural glutaminyl amber suppressor strain XL1-Blue was $2 \times 10^{11}$ plaque-forming units per milliliter of culture (PFU/mL). The yield of M13KE-SBP phage in E. coli TTS/RS 3 in the presence of 2 mM p-acetylphenylalanine 3 is comparable to that produced in XL1-Blue and is dependent on the presence of p-acetylphenylalanine 3. In the presence of this unnatural amino acid, the phage yield is $1.8 \times 10^{11}$ PFU/mL; in the absence of the unnatural amino acid the phage yield is reduced by 81-fold (see FIG. 4). In a large-scale phage preparation, a difference in yield of over 1000-fold was obtained. The phage yield experiments were carried out with five E. coli TTS/RS cell lines that incorporate five distinct unnatural amino acids. These were: O-methyltyrosine 1, p-azidophenylalanine 2, p-acetylphenylalanine 3, p-benzoylphenylalanine 4, and 3-(2-naphthyl)alanine 5 (see FIG. 3). A similar dependence on the presence of the unnatural amino acid for phage yield was observed in each system (see FIG. 4), indicating that this phage-display scheme is likely to be general for a large number of unnatural amino acids.

Example 2

Plasmid Constructions

The present Example describes the construction of the plasmids used to expresses the orthogonal tRNA and orthogonal aminoacyl tRNA synthetase in E. coli host cells.

Construction of Plasmid pDULE/CM

Plasmid pDULE with an ampicillin resistant marker was digested with Bsm I and treated with Mung Bean nuclease to create a blunt end. The resulting DNA was digested with Cla I and purified by agarose gel electrophoresis. The chloramphenicol acetyltransferase gene was amplified from plasmid pACYC184 (NEB) by PCR using the primers:

| Primer | Sequence | SEQ ID NO: |
|---|---|---|
| FT18 | 5'-GACAGCTTATCATCGATGAGACGTTGATCGGCACGTAAG | 12 |
| FT19 | 5'-GGTTGGTTTGCGCATTCAGCGCTAACCGTTTTATCAGGC | 13 |

The PCR product was digested with Cla I and ligated with the pDULE to give pDULE/CM. The TTS cell line was generated by transformation of plasmid pDULE/CM into Top 10 F' (Invitrogen).

Construction of pM13KE-SBP Plasmid:

The streptavidin binding peptide pIII fusion was prepared using extension

```
primer FT121:
                                       (SEQ ID NO:14)
5'-CATGCCCGGGTACCTTTCTATTCTC
and template FT126:
                                       (SEQ ID NO:15)
5'-CATGTTTCGGCCGAGCCCCCACCCTGCGGATGAGCCAGCAAAGTCTA

GCCGGCAGAGTGAGAATAGAAAGGTACCCGGG;
``` digested with Eag I and Acc65 I. Insertion of this fragment into plasmid pM13KE (New England BioLabs) between the Eag I and Acc65 I sites with T4 ligase yielded pM13KE-SBP. The ligation product was transformed into XL1-Blue and plated on LB plates with an XL1-Blue cell lawn in the presence of 20 µg/mL IPTG and 20 µg/mL XGal to generate blue phage plaques.

Example 3

Phage Culture and Phage Titering Protocols

The present Example describes the general methodologies of phage culture and titering as used herein.

General Phage Production Protocol in *E. coli* XL1-BLUE

A single phage plaque was added to 10 mL of 2×YT containing mid-log *E. coli* strain XL1-Blue and 12 µg/mL of tetracycline. After incubation at 37° C. for 5 hrs, the culture was centrifuged at 6000× g, at 4° C. for 5 min. Phage was precipitated from the supernatant with 20% volume PEG buffer (20% PEG 8000, 2.5 M NaCl). The mixture was kept at 4° C. overnight and centrifuged at 10,000× g for 10 min at 4° C. The phage pellet was dissolved in 500 µL of 1× PBS, pH 7.4, centrifuged at 20,000× g for 10 min at 4° C. to remove the remaining cell debris, and stored at 4° C.

General Phage Production Protocol in *E. coli* TTS

A single phage plaque was added to 10 ml of 2×YT containing mid-log TTS and 12 µg/mL of tetracycline, 34 µg/mL chloramphenicol and 2 mM of appropriate unnatural amino acid. The rest of the protocol is the same as the general phage production protocol in *E. coli* XL1-Blue.

General Plaque Formation and Phage Titer Experiment

After a series of 10 fold dilutions in microtiter plates, 5 µl of both M13KE wild type and M13KE-SBP phages were plated on LB Agar plates with a TTS/RS 3 cell lawn supplemented with 20 µg/mL IPTG, 20 µg/mL XGal, 12 µg/mL tetracycline, 34 µg/mL chloramphenicol and 2 mM of the corresponding unnatural amino acid. The plates were incubated at 37° C. overnight.

Phage Titer

After a series of 10 fold dilutions in microtiter plates, 5 µL of phage were plated on LB agar plates with an XL1-Blue cell lawn supplemented with 20 µg/mL IPTG, 20 µg/mL XGal, and 12 µg/mL tetracycline. The plates were incubated at 37° C. overnight.

Example 4

Covalent Conjugation of Phage Displayed Polypeptides Comprising p-azido-L-phenylalanine using a [3+2] Cycloaddition Reaction The present Example describes the covalent modification of a phage-displayed polypeptide comprising p-azido-L-phenylalanine. This covalent modification uses a [3+2] cycloaddition reaction to conjugate an alkyne-containing moiety to the p-azido-L-phenylalanine, resulting in a triazole linkage between the polypeptide and the alkyne-containing moiety. FIG. 15 provides the general reaction chemistry of the [3+2] cycloaddition reaction.

M13KE-SBP phage were produced in *E. coli* TTS/RS 2 in the presence of 2 mM p-azidophenylalanine 2. The resulting phage were then conjugated with the alkyne-derivatized fluorescein dye shown in FIG. 5, structure 6 (Deiters et al., *J. Am. Chem. Soc.* (2003) 125:11782-11783) by a highly specific azide-alkyne [3+2] cycloaddition (Rostovtsev et al., *Angew. Chem. Int. Ed.* (2002) 41:2596-2599). Phage prepared in XL1-Blue were used as a negative control.

Specifically, the cycloaddition conjugation reactions between phage and alkyne derivatized fluorescein dye 6 were conducted as follows. Phage from a stock solution (50 µL, about $10^{11}$ PFU) was precipitated by PEG and dissolved in 90 µL of 100 µM potassium phosphate buffer (PB), pH 8.0. The phage solution was supplemented with 5 µL of tert-butanol, 2 mM tris(carboxyethyl)phosphine (TCEP), 2 mM tris(triazolyl) amine ligand, 2 mM fluorescein dye 6 and 1 mM $CuSO_4$. The final reaction volume was 100 µL. Upon the addition of tris(triazolyl) amine ligand, phage precipitated. The reaction mixture was incubated at 4° C. for 16 hours and was centrifuged at 20,000× g for 10 min. Phage precipitated completely under the reported conditions [2 mM tris(carboxyethyl)phosphine (TCEP), 2 mM tris-(triazolyl) amine ligand, 2 mM fluorescein dye 6 and 1 mM CuSO4 in potassium phosphate buffer (PB) at pH 8.0 with 5% tert-butyl alcohol as cosolvent] (see, Wang et al., *J. Am. Chem. Soc.* (2003) 125:3192-3193). Replacement of TCEP with Cu wire provided no improvement. Precipitation was minimized when diluted reagents were used (0.1 mM TCEP, 0.2 mM ligand, 0.2 mM fluorescein dye 6 and 0.1 mM $CUSO_4$ in PB buffer at pH 8.0). See, Link and Tirrell, *J. Am. Chem. Soc.* (2003) 125:11164-11165.

After conjugation, the reaction mixture was dialyzed and subjected to SDS-PAGE and Western blot analysis (see FIG. 6). The Western analysis used both anti-fluorescein (part I) and anti-pIII (part II) primary antibodies to verify the identity of the separated protein species. Specifically, both precipitant and concentrated supernatant from the previous cycloaddition reaction were electrophoresed by 4-20% SDS-PAGE gel (Invitrogen) and transferred to a nitrocellulose membrane (semidry 20 V, 20 min). The membrane was blocked with 5% skim milk in 1×PBS at 4° C. overnight and incubated with a 1/1000 dilution of anti-fluorescein rabbit IgG (Molecular Probes) at room temperature for 2 hours. The membrane was washed and then probed with 1/10,000 dilution of anti-rabbit mouse IgG-alkaline phosphatase conjugate (Sigma). The membrane was washed six times with PBST (PBS, 0.5% Tween-20), developed with ECF (Amersham Biosciences) and scanned using a phosphor imager. An anti-pIII western analysis was also conducted, where anti-pIII mouse IgG (MoBiTec) was used as the primary antibody. Anti-mouse AP conjugate was used as the secondary antibody.

Development of these blots (see FIG. 6, part I) revealed that the fluorescein conjugate was detected as a single band only in the case of phage produced in TTS/RS 2 supplemented with 2 mM p-azidophenylalanine 2 (lane a), in contrast to phage produced in XL-1 Blue *E. coli* (lane b). The identity or this band was further confirmed as the pIII minor coat protein by the anti-pE Western blot analysis (part II). These results demonstrate that the unnatural amino acid is incorporated specifically into the pm coat protein of the unnatural phage.

Example 5

Preservation of Biological Activity of a Phage Displayed Polypeptide Comprising the Unnatural Amino Acid p-azido-L-phenylalanine The present Example illustrates the preservation of biological activity of the phage-displayed streptavidin binding peptide (SBP) fusion comprising p-azido-L-phenylalanine. The streptavidin binding activity was assayed in the phage preparations.

To demonstrate that the mutant streptavidin binding peptide presented on the N-terminus of the pIII protein is functional, a phage-binding enzyme-linked immunosorbent assay (ELISA) was utilized. This system used M13KE-SBP phage prepared in TTS/RS 2 and TTS/RS 3 cells supplemented with 2 mM p-azidophenylalanine 2 or p-acetylphenylalanine 3, respectively (see the data in FIG. 7 and corresponding graph in FIG. 8). M13KE-SBP phage prepared in XL1-Blue served as a positive control, while the wild-type M13KE phage served as a negative control.

In this analysis, streptavidin coated microtiter plates (Pierce) were blocked with 300 µL of either 4% BSA in 1×PBS, or 4% BSA in 1×PBS with 10 µM biotin at 4° C. overnight. Following washing, 100 µL of either M13KE phage ($10^{11}$ PFU), M13KE-SBP phage prepared in *E. coli* XL1-Blue, M13KE-SBP prepared in TTS/RS 2 or TTS/RS 3 with 2 mM of the corresponding unnatural amino acid were added to the wells with four-fold serial dilution. After incubation at room temperature for two hours, the wells were washed with 200 µL PBST three times and incubated with a 1/10,000 dilution of anti-M13 HRP conjugate (Amersham Biosciences) for one hour. Following ten washes with 200 µL PBST, the wells were developed with 100 µL OPD substrate in stable peroxidase buffer (Pierce). The reaction was terminated by addition of 100 µL 2.5 N $H_2SO_4$. The $OD_{492\ nm}$ of each well was recorded with a plate reader (see FIG. 7). The value of each point in the table shown in FIG. 7 is the average of three experiments. The error is less than 10%.

This data is shown graphically in FIG. 8. This figure shows that M13KE-SBP phage prepared in TTS/p-azidophenylalanine 2 and TTS/p-acetylphenylalanine 3 bind to streptavidin more strongly than the positive control phage prepared in XL1-Blue. This increase in observed affinity might result from increased binding affinity or proteolytic stability of the displayed peptide containing the unnatural amino acids.

In a model phage selection experiment, wild-type phage and phage carrying the mutant SBP with p-azido-L-phenylalanine were exposed to streptavidin coated wells, followed by recovery of the bound phage. Titer of the recovered enriched phage following elution was used as a measure of the binding specificity of the page for the streptavidin.

Specifically, two wells from a streptavidin coated microtiter plate (Pierce) were blocked with 300 µL of 4% BSA in 1×PBS at 4° C. overnight. After washing, separate streptavidin coated wells were incubated with similar numbers of phage (each in 100 µL) of either M13KE-SBP prepared in TTS/RS 3 or M13KE wild type phage at room temperature for 2 hours and washed 10 times with 200 µL PBST. The bound phage was eluted from the plate solid support with 10 µM biotin 1×PBS, pH 7.4. The input and output phage were titered (see, FIG. 9).

The recovery rate of M13KE-SBP phage prepared in TTS/RS 3 is $9 \times 10^3$ fold over that of M13KE wild-type phage (FIG. 9). These experimental results show that the mutant SBP is displayed on phage and is functional (i.e., retains the ability to specifically bind strepavidin).

The generalization of phage display to include unnatural amino acids should significantly increases the scope of phage display technology. For example, the incorporation unnatural amino acids into phage-displayed polypeptides can lead to increased binding affinity and specificity, conformationally constrained backbones and side chains, and enhanced proteolytic stability. Unnatural amino acids can provide reactive sites for the conjugation of nonpeptidic molecules as well as photoaffinity labels for the identification of orphan ligands or receptors. Finally, this methodology is also applicable to other display formats such as ribosome and yeast display.

Example 6

Selective Covalent Modification of Phage Displayed Polypeptides Comprising p-azido-L-phenylalanine Using the Staudinger Ligation Reaction The present Example illustrates the selective covalent modification of phage-displayed polypeptides comprising p-azido-L-phenylalanine using the Staudinger ligation reaction. This Example used the phage-displayed streptavidin binding peptide (SBP)/pIII fusion protein described in Example 1 as the substrates for the Staudinger reaction, as illustrated in FIG. 10.

As described in Examples 1-3, a phage display system was created in which the streptavidin binding peptide (SBP), AGXTLLAHPQ (SEQ ID NO: 11), was displayed pentavalently as a fusion to the pIII protein of M13 filamentous phage. The N-terminal AG sequence facilitates cleavage of the signal peptide; the third residue, X, encoded by the amber nonsense codon TAG, designates the unnatural amino acid to be incorporated. The phage Ph-Az (encoding SBP with p-azido-L-phenylalanine 2 at residue X) was prepared in *E. coli* strain TTS/RS in the presence of 2 mM p-azido-L-phenylalanine 2 with good efficiency and high fidelity. *E. coli* TTS/RS contains a plasmid that constitutively expresses a *Methanococcus jannaschii* mutant amber suppressor $tRNA_{CUA}^{Tyr}$ ($mutRNA_{CUA}^{Tyr}$) and a mutant *M. jannaschii* tyrosyl-tRNA synthetase (MjTyrRS) which specifically charges $mutRNA_{CUA}^{Tyr}$ with p-azido-L-phenylalanine 2. As a negative control, another SBP displayed phage (Ph-Q) was prepared in *E. coli* XL1-Blue, a natural amber suppression strain that incorporates glutamine at residue X.

Using this phage system, the feasibility of using phage displayed polypeptides comprising the unnatural amino acid p-azido-L-phenylalanine 2 as a substrate for a selective Staudinger modification was examined. The fluorescein-derived phosphines 7 and 8 (see the structures in FIG. 10) were used for the Staudinger ligation reaction since they can be easily detected.

Compound 7 was synthesized following published procedures (Saxon and Bertozzi, *Science* 2000, 287, 2007-2010; Wang et al., *Bioconjugate Chem.* 2003, 14, 697-701). Compound 8 was prepared by the coupling reaction of 2-(diphenylphosphino)phenol (74 mg, 0.27 mmol), see Suárez et al., *Organometallics* 2002, 21, 4611-4621, and 5(6)-carboxyfluorescein (100 mg, 0.27 mmol) in the presence of dicyclohexylcarbodiimide (62 mg, 0.3 mmol) in anhydrous DMF (1 mL) at ambient temperature for 12 hrs, and purified using preparative TLC as a red powder (3 mg, 2%); HRMS (ESI-TOF): $C_{39}H_{24}O_7P_1$ [M−1]⁻ calcd: 635.1265; found 635.1248.

According to the scheme in FIG. 10, phosphine 7 can react with phage Ph-Az to form an aza-ylide intermediate (Staudinger and Meyer, *Helv. Chim. Acta* 1919, 2, 635-646), followed by intramolecular cyclization (Saxon and Bertozzi, *Science* 2000, 287, 2007-2010) to ultimately yield a fluorescein labeled phage product. The conjugation of 8 with Ph-Az should undergo a traceless Staudinger ligation by a similar reaction mechanism to yield a fluorescein-labeled phage without an intervening triphenylphosphine oxide group.

Conjugation reactions between the phage molecules and the phosphines 7 and 8 were carried out between phage Ph-Az and triphenylphosphines 7 and 8 with approximately $10^{11}$ phage particles and 0.01 mM phosphine in 10 mM phosphate buffered saline solution (PBS, pH 7.4); similar reactions were carried out with phage Ph-Q as a negative control. A stock (0.5 mM) of each phosphine reactant was prepared in DMF, and was diluted with reaction buffer to a final concentration of 0.01 mM and total volume of 50 μL. The ligation reactions were carried out at ambient temperature with shaking for 16 hrs. The reaction mixture was then dialyzed against PBS and subjected to subsequent analysis.

Figure 11:
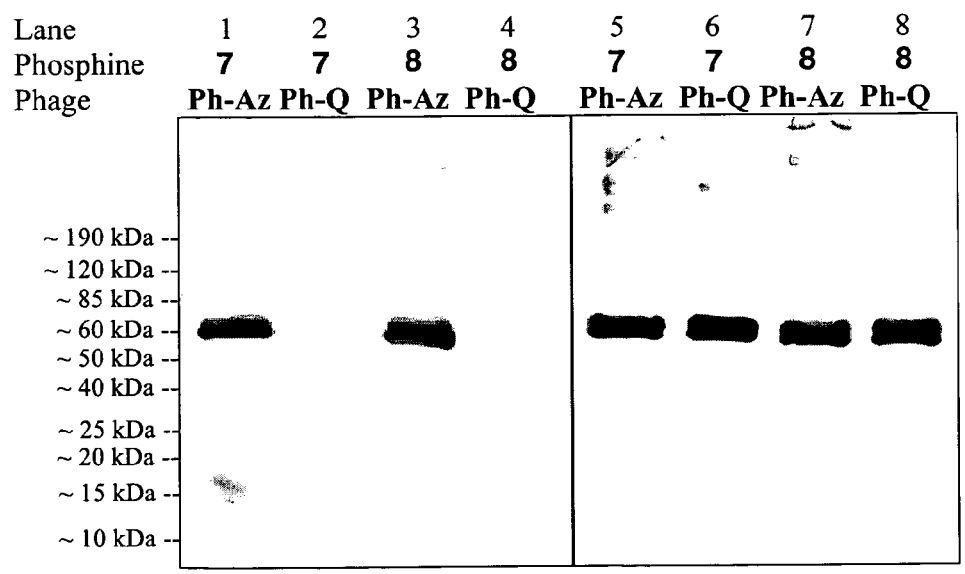
FIG. 11 provides a chemiluminescence image of a Western blot analysis of phage Ph-Az and Ph-Q after Staudinger ligation with phosphines 7 and 8. The analysis used anti-fluorescein primary antibody (lanes 1-4) or anti-pIII primary antibody (lanes 5-8).

The ligation reaction products were analyzed by Western blotting (see FIG. 11) using the protocol described in Example 4. The fluorescein conjugates were observed as a single band using an anti-fluorescein primary antibody (lanes 1-4) only from the ligation of Ph-Az with either phosphine 7 or 8, and not observed in the case of control reactions using Ph-Q. This band was further identified as the pIII minor coat protein by using an anti-pIII antibody in the analysis (lanes 5-8). These results clearly show a high degree of selectivity between phosphine 7 or 8 and the azide containing phage peptide.

Example 7

Preservation of Phage Viability Following Selective Staudinger Modification of a Phage-displayed Polypeptide The present Example illustrates the preservation of phage viability following selective Staudinger modification of a phage-displayed polypeptide comprising p-azido-L-phenylalanine.

To show that the Staudinger coupling reaction does not lead to a loss of infective phage particles, phage viability was determined by titering phage Ph-Az before and after the Staudinger ligation with 7 or 8. The observed number of viable phage particles from a Staudinger reaction mixture was $(1.7\pm1)\times10^{11}$ plaque-forming units per milliliter (PFU/mL), compared to $(2.5\pm1)\times10^{11}$ PFU/mL determined from control solutions without phosphine 7 or 8.

Example 8

Phage Selection Following Staudinger Modification of a Phage-displayed Polypeptide The present Example illustrates the selection of phage following the Staudinger modification of a phage-displayed polypeptide. The selection utilized an immobilized anti-fluorescein antibody to retain phage that comprised a conjugated phosphine 7, which would be present only if the Staudinger modification was successful. The phage titering also revealed phage viability.

In a model phage selection/enrichment experiment, a similar number of phage particles prepared from the aforementioned Staudinger ligation of phosphine 7 with Ph-Az and Ph-Q were incubated in separate wells which were pre-coated with anti-fluorescein antibody. After iterative washing, the bound phage was eluted with 0.05% BSA-FITC conjugate and titered.

More specifically, anti-fluorescein antibody (20 μg/mL, 250 μL/well) was coated in aqueous $Na_2CO_3$ (0.1 M, pH 9.6) onto eight wells of an immuno-plate (Fisher) at 37° C. for 4 hrs. Wells were washed (3×0.9% NaCl-0.05% Tween 20), blocked overnight with BSA (0.5%) at 4° C., and then incubated at room temperature for 5 hrs with phage (100 μL) either from a ligation reaction or a control solution. After being washed, the phage was eluted from the plate with BSA-FITC conjugate (0.05%). The recovered phage was titered.

The input phage titers were as follows: Ph-Az: $1.0\times10^9$ PFU; and Ph-Q: $2.0\times10^9$ PFU. The output phage titers were Ph-Az: $1.2\times10^6$ PFU; and Ph-Q: $1.0\times10^4$ PFU. The recovery rate of fluorescein labeled phage derived from the ligation of Ph-Az with 7 (0.12%) is 120 fold greater than that of the control phage derived from Ph-Q (0.001%).

These results from Examples 7 and 8 demonstrate that the Staudinger ligation reaction does not significantly affect phage viability. In contrast, it is important to note that phage Ph-Az are nonviable after exposure to the reaction conditions in the [3+2] cycloaddition with a terminal alkyne group and copper catalyst. Also see, e.g., Rostovtsev et al., *Angew. Chem.* 2002, 114, 2708-2711; and *Angew. Chem. Int. Ed.* 2002, 41, 2596-2599. It was found that the copper catalyst is predominantly responsible for the viability loss; however, addition of high concentrations of EDTA during the dialysis step did not notably improve phage viability.

Example 9

Characterization of Staudinger Modification Reaction Products

To further characterize the Staudinger ligation products and determine the conjugation efficiency, a representative Z-domain protein (Wang et al., *Proc. Natl. Acad. Sci. U.S.A.* 2003, 100, 56-61) containing p-azido-L-phenylalanine 2 at residue 7 was expressed in an *E. coli* strain using mutRNA$_{CUA}^{Tyr}$ (SEQ ID NO: 1) and the mutant MjTyrRS (see, FIG. 1, SEQ ID NO: 4) that selectively charges the tRNA with p-azido-L-phenylalanine 2 (see Wang et al., *Science* 2001, 292, 498-500; Wang and Schultz, *Angew. Chem.* 2005, 117, 34-68; *Angew. Chem. Int. Ed.* 2005, 44, 34-66; and Chin et al., *J. Am. Chem. Soc.* 2002, 124, 9026-9027). Further general description of the expression of the Z-domain polypeptide can be found in Wang et al., *Proc. Natl. Acad. Sci. U.S.A.* 2003, 100, 56-61. This azide-containing Z-domain was purified and conjugated with phosphines 7 or 8.

For this conjugation reaction, a stock (10 mM) of each phosphine reactant was prepared in DMF, and was diluted with reaction buffer containing mutant Z-domain protein (0.1 mM) to a final concentration of 1 mM and total volume of 10 μL. The ligation reactions were carried out in phosphate buffered saline solution (PBS, pH 7.4) at ambient temperature with shaking for 16 hrs. The reaction mixture was then passed through a PD-10 column, eluted in water, dialyzed and analyzed by MALDI-TOF spectroscopy.

Figure 12:
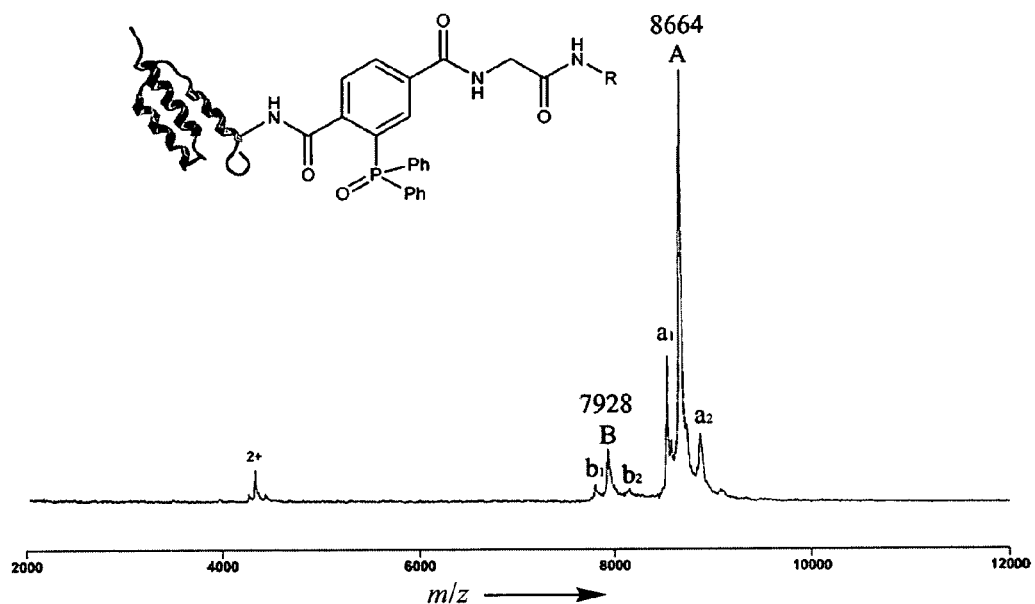
FIG. 12 provides a MALDI-TOF analysis of the reaction products from the Staudinger ligation of p-azido-L-phenylalanine 2 containing Z-domain protein with phosphine 7. Peaks A and B can be assigned to the conjugation and reduction product, respectively; minor peaks $a_2$, $b_2$, $a_1$ and $b_1$ are derived from the matrix-adducts and the exclusion of methionine from A and B.

The major peaks of the observed spectra match the expected Staudinger ligation products when using the phosphine 7 as the conjugated moiety (see FIG. 12). Peak A is assigned to the Staudinger ligation product: $C_{386}H_{556}N_{107}O_{119}S_1P_1$, calcd: 8662; found: 8664. Peak B is assigned to the reduction product via classical Staudinger reaction: $C_{344}H_{529}N_{105}O_{110}S_1$, calcd: 7928; found: 7928. Minor peaks $a_1$ and $b_1$, corresponding to A and B, are assigned to the products derived from mutant Z-domain protein without the first methionine. Minor peaks $a_2$ and $b_2$, corresponding to A and B, are from the matrix adduct. No azide-containing Z-domain was observable (<1%), indicating that the reaction proceeds in high yield. For the Staudinger ligation of phosphine 7, the conjugation efficiency is estimated to be >90% based on the integration ratio of the peaks in the MALDI-TOF spectrum.

Figure 13:
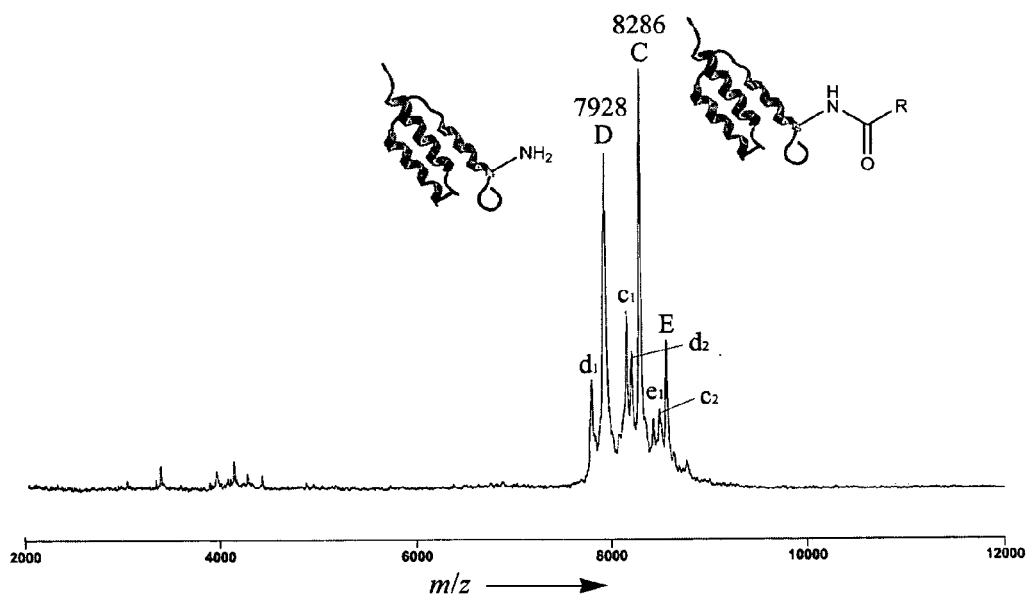
FIG. 13 provides a MALDI-TOF spectral analysis of the reaction products from the Staudinger ligation of pAzPhe containing Z-domain protein with phosphine 8.

FIG. 13 shows a MALDI-TOF analysis of the reaction products from the Staudinger ligation of mutant Z-domain protein with phosphine 8. Peak C is assigned to traceless Staudinger ligation product: $C_{365}H_{539}N_{105}O_{116}S_1$, calcd: 8286; found 8286. Peak D is assigned to the reduction product via classical Staudinger reaction: $C_{344}H_{529}N_{105}O_{110}S_1$, calcd: 7928; found: 7928. Peak E is assigned to the aza-ylide intermediate: $C_{383}H_{552}N_{105}O_{117}S_1P_1$, calcd: 8562; found: 8563. Minor peaks $c_1$, $d_1$ and $e_1$, corresponding to C, D and E, are assigned to the products derived from mutant Z-domain protein without the first methionine. Minor peaks $c_2$ and $d_2$, corresponding to C and D, are from the matrix adduct.

In contrast to the Staudinger ligation of phosphine 7, the traceless Staudinger ligation of phosphine 8 afforded a lower yield of ~50%. The lower conjugation efficiency of 8 may be due to a slower ligation rate, presumably in the intramolecular cyclization step (Saxon and Bertozzi, *Org. Lett.* 2000, 2, 2141-2143) and the ease of the hydrolysis of phenol ester in 8. These would lead to an amine product as in the classical Staudinger reactions (Saxon and Bertozzi, *Science* 2000, 287, 2007-2010; and Staudinger and Meyer, *Helv. Chim. Acta* 1919, 2, 635-646).

Doping experiments with authentic material demonstrated that the p-azido-L-phenylalanine 2 Z-domain mutant is stable. FIG. 14 provides a MALDI-TOF analysis of the reaction products from the Staudinger ligation of p-azido-L-phenylalanine 2 containing Z-domain protein with phosphine 7 and doping with comparative amount of authentic p-azido-L-phenylalanine 2 Z-domain mutant.

In summary, it is shown herein that model Staudinger ligations between fluorescein-tethered phosphines and either a p-azido-L-phenylalanine 2 containing phage-displayed peptide or a mutant Z-domain protein occur with excellent selectivity and efficiency. The Staudinger ligation does not affect phage viability so that after the completion of ligation enrichment can be performed without difficulty. This work provides useful methods for selectively modifying proteins without altering their function and should be useful for the generation of highly homogenous PEGylated proteins, surface immobilized proteins or proteins modified with spectroscopic or affinity reagents.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

---

What is claimed is:

1. A purified or isolated phage comprising a phage-displayed polypeptide, wherein the polypeptide comprises an unnatural amino acid that comprises:

a)

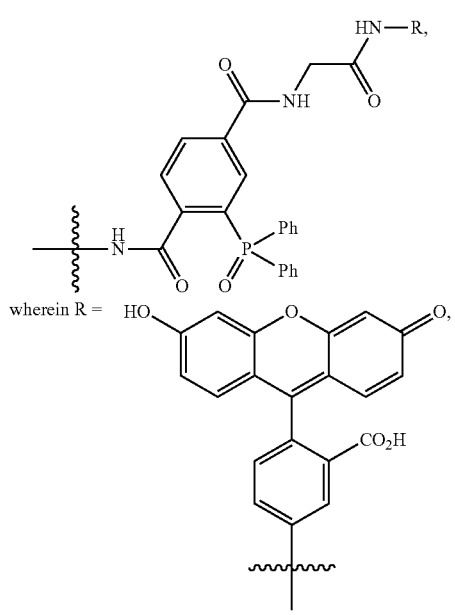

and wherein the purified or isolated phage is viable;

b)

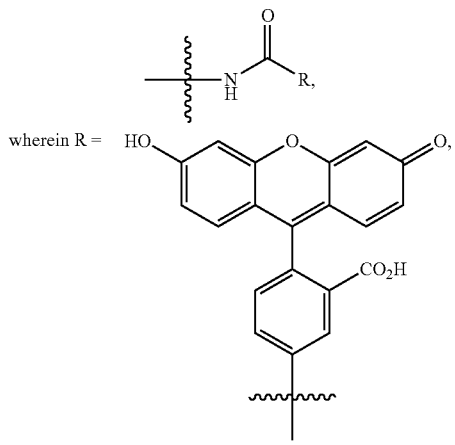

and wherein the purified or isolated phage is viable;

or, c)

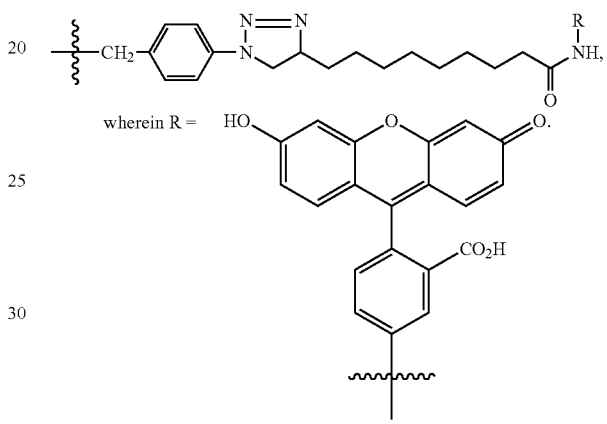

2. A purified or isolated phage comprising a polypeptide, wherein the polypeptide comprises an unnatural amino acid residue selected from the group consisting of:
   a) an unnatural amino acid residue comprising an amide moiety and a phosphine oxide moiety, wherein the phage is viable, and
   b) an unnatural amino acid residue comprising a triazole linkage.

3. A purified or isolated post-translationally modified phage produced by a process comprising the steps of:
   a) providing a phage comprising a polypeptide, wherein the polypeptide comprises a p-propargyloxyphenylalanine or a p-azidophenylalanine;
   b) reacting the p-propargyloxyphenylalanine or p-azidophenylalanine acid via Staudinger ligation or [3+2] cycloaddition; and
   c) producing the purified or isolated post-translationally modified phage by covalent modification of the p-propargyloxyphenylalanine or p-azidophenylalanine acid;
   wherein the purified or isolated post-translationally modified phage is viable when the p-propargyloxyphenylalanine or p-azidophenylalanine acid is reacted via Staudinger ligation.

4. The phage of claim 1, 2, or 3, wherein said phage is a filamentous phage.

5. The phage of claim 1, 2, or 3, wherein said phage is a recombinant M13 phage.

6. The phage of claim 1, 2, or 3, wherein said polypeptide is a phage-displayed fusion polypeptide.

7. The phage of claim 6, wherein said fusion polypeptide comprises a peptide linker that comprises an amino acid sequence that can be recognized and cleaved by a protease.

8. The phage of claim 7, wherein said protease is selected from Factor Xa, Factor XIa, Kallikvein, thrombin, Factor XIIa, collagenase and enterokinase.

9. The phage of claim 3, wherein said aryl-azide unnatural amino acid residue is a para-azido-L-phenylalanine residue.

10. The phage of claim 1, 2, or 3, wherein said phage or said polypeptide is immobilized to a solid support.

* * * * *

UNITED STATES PATENT AND TRADEMARK OFFICE
CERTIFICATE OF CORRECTION

PATENT NO. : 8,586,340 B2
APPLICATION NO. : 11/580223
DATED : November 19, 2013
INVENTOR(S) : Tsao et al.

It is certified that error appears in the above-identified patent and that said Letters Patent is hereby corrected as shown below:

In the Specification

Column 1, Lines 14-21, the paragraph STATEMENT AS TO RIGHTS OF INVENTIONS MADE UNDER FEDERALLY SPONSORED RESEARCH AND DEVELOPMENT should be changed to:
-- STATEMENT OF GOVERNMENT LICENSE RIGHTS
This invention was made with government support under grant number GM056528 awarded by the National Institutes of Health and under grant number DE-FG03-00ER46051 awarded by the United States Department of Energy. The government has certain rights in the invention. --

Signed and Sealed this
Seventh Day of April, 2020

Andrei Iancu
*Director of the United States Patent and Trademark Office*

SEQUENCE LISTING

<160> NUMBER OF SEQ ID NOS: 15

<210> SEQ ID NO 1
<211> LENGTH: 77
<212> TYPE: RNA
<213> ORGANISM: Artificial Sequence
<220> FEATURE:
<223> OTHER INFORMATION: mutant Methanococcus jannaschii suppressor
      tyrosyl-tRNA-CUA

<400> SEQUENCE: 1
ccggcgguag uucagcaggg cagaacggcg gacucuaaau ccgcauggcg cugguucaaa      60
uccggcccgc cggacca                                                    77

<210> SEQ ID NO 2
<211> LENGTH: 306
<212> TYPE: PRT
<213> ORGANISM: Methanococcus jannaschii

<400> SEQUENCE: 2

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 3
<211> LENGTH: 918
<212> TYPE: DNA
<213> ORGANISM: Methanococcus jannaschii

<400> SEQUENCE: 3
atggacgaat ttgaaatgat aaagagaaac acatctgaaa ttatcagcga ggaagagtta       60
agagaggttt taaaaaaaga tgaaaaatct gcttacatag gttttgaacc aagtggtaaa      120
atacatttag gcattatctc caaataaaa agatgattg atttacaaaa tgctggattt        180
gatataatta tattgttggc tgatttacac gcctatttaa accagaaagg agagttggat      240
gagattagaa aaataggaga ttataacaaa aagttttttg aagcaatggg gttaaaggca      300
aaatatgttt atggaagtga attccagctt gataaggatt atacactgaa tgtctataga      360
ttggctttaa aaactacctt aaaaagagca agaaggagta tggaacttat agcaagagag      420
gatgaaaatc caaaggttgc tgaagttatc tatccaataa tgcaggttaa tgatattcat      480
tatttaggcg ttgatgttgc agttggaggg atggagcaga gaaaaataca catgttagca      540
agggagcttt taccaaaaaa ggttgttgt attcacaacc ctgtcttaac gggtttggat       600
ggagaaggaa agatgagttc ttcaaaaggg aatttttatag ctgttgatga ctctccagaa     660
gagattaggg ctaagataaa gaaagcatac tgcccagctg gagttgttga aggaaatcca     720

```
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gatttagag    900 ccaattagaa agagatta                                                  918
```

<210> SEQ ID NO 4
<211> LENGTH: 306
<212> TYPE: PRT
<213> ORGANISM: Artificial Sequence
<220> FEATURE:
<223> OTHER INFORMATION: p-azido-L-phenylalanine aminoacyl-tRNA
      synthetase clone-1 amino acid sequence (derived from wild-type
      Methanococcus jannaschii tyrosyl tRNA-synthetase)

<400> SEQUENCE: 4

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

```
<210> SEQ ID NO 5
<211> LENGTH: 306
<212> TYPE: PRT
<213> ORGANISM: Artificial Sequence
<220> FEATURE:
<223> OTHER INFORMATION: p-azido-L-phenylalanine aminoacyl-tRNA
      synthetase clone-2 amino acid sequence (derived from wild-type
      Methanococcus jannaschii tyrosyl tRNA-synthetase)

<400> SEQUENCE: 5
```

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

```
<210> SEQ ID NO 6
<211> LENGTH: 306
<212> TYPE: PRT
<213> ORGANISM: Artificial Sequence
<220> FEATURE:
<223> OTHER INFORMATION: p-azido-L-phenylalanine aminoacyl-tRNA
      synthetase clone-3 amino acid sequence (derived from wild-type
      Methanococcus jannaschii tyrosyl tRNA-synthetase)
```

```
<400> SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 7
<211> LENGTH: 306
<212> TYPE: PRT
<213> ORGANISM: Artificial Sequence
<220> FEATURE:
<223> OTHER INFORMATION: p-azido-L-phenylalanine aminoacyl-tRNA
      synthetase clone-4 amino acid sequence (derived from wild-type
      Methanococcus jannaschii tyrosyl tRNA-synthetase)

<400> SEQUENCE: 7

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30
```

```
Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
               100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 8
<211> LENGTH: 306
<212> TYPE: PRT
<213> ORGANISM: Artificial Sequence
<220> FEATURE:
<223> OTHER INFORMATION: p-azido-L-phenylalanine aminoacyl-tRNA
      synthetase clone-5 amino acid sequence (derived from wild-type
      Methanococcus jannaschii tyrosyl tRNA-synthetase)

<400> SEQUENCE: 8

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80
```

```
Glu Ile Arg Lys Ile Gly Asp Tyr Asn Lys Lys Val Phe Glu Ala Met
                 85                  90                  95
Gly Leu Lys Ala Lys Tyr Val Tyr Gly Ser Arg Phe Gln Leu Asp Lys
                100                 105                 110
Asp Tyr Thr Leu Asn Val Tyr Arg Leu Ala Leu Lys Thr Thr Leu Lys
            115                 120                 125
Arg Ala Arg Arg Ser Met Glu Leu Ile Ala Arg Glu Asp Glu Asn Pro
        130                 135                 140
Lys Val Ala Glu Val Ile Tyr Pro Ile Met Gln Val Asn Val Ile His
145                 150                 155                 160
Tyr Asp Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
                180                 185                 190
Asn Pro Val Leu Thr Gly Leu Asp Gly Glu Gly Lys Met Ser Ser Ser
            195                 200                 205
Lys Gly Asn Phe Ile Ala Val Asp Asp Ser Pro Glu Glu Ile Arg Ala
        210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
                260                 265                 270
Leu Glu Ser Leu Phe Lys Asn Lys Glu Leu His Pro Met Asp Leu Lys
            275                 280                 285
Asn Ala Val Ala Glu Glu Leu Ile Lys Ile Leu Glu Pro Ile Arg Lys
        290                 295                 300
Arg Leu
305

<210> SEQ ID NO 9
<211> LENGTH: 306
<212> TYPE: PRT
<213> ORGANISM: Artificial Sequence
<220> FEATURE:
<223> OTHER INFORMATION: p-azido-L-phenylalanine aminoacyl-tRNA
      synthetase clone-6 amino acid sequence (derived from wild-type
      Methanococcus jannaschii tyrosyl tRNA-synthetase)

<400> SEQUENCE: 9

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Gly
                20                  25                  30
Ile Gly Phe Glu Pro Ser Gly Lys Ile His Leu Gly His Tyr Leu Gln
            35                  40                  45
Ile Lys Lys Met Ile Asp Leu Gln Asn Ala Gly Phe Asp Ile Ile Ile
        50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Thr Phe Gln Leu Asp Lys
                100                 105                 110
Asp Tyr Thr Leu Asn Val Tyr Arg Leu Ala Leu Lys Thr Thr Leu Lys
            115                 120                 125
```

```
Arg Ala Arg Arg Ser Met Glu Leu Ile Ala Arg Glu Asp Glu Asn Pro
            130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                    165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
290                 295                 300

Arg Leu
305

<210> SEQ ID NO 10
<211> LENGTH: 306
<212> TYPE: PRT
<213> ORGANISM: Artificial Sequence
<220> FEATURE:
<223> OTHER INFORMATION: p-azido-L-phenylalanine aminoacyl-tRNA
      synthetase clone-7 amino acid sequence (derived from wild-type
      Methanococcus jannaschii tyrosyl tRNA-synthetase)

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gln Ile His
145                 150                 155                 160

Ser Ser Gly Val Asp Val Ala Val Gly Gly Met Glu Gln Arg Lys Ile
                165                 170                 175
```

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 11
<211> LENGTH: 10
<212> TYPE: PRT
<213> ORGANISM: Artificial Sequence
<220> FEATURE:
<223> OTHER INFORMATION: pIII fusion streptavidin binding peptide (SBP)
<220> FEATURE:
<221> NAME/KEY: MISC_FEATURE
<222> LOCATION: (3)..(3)
<223> OTHER INFORMATION: X is an unnatural amino acid

<400> SEQUENCE: 11

Ala Gly Xaa Thr Leu Leu Ala His Pro Gln
1               5                   10

<210> SEQ ID NO 12
<211> LENGTH: 39
<212> TYPE: DNA
<213> ORGANISM: Artificial Sequence
<220> FEATURE:
<223> OTHER INFORMATION: FT18 PCR primer

<400> SEQUENCE: 12
gacagcttat catcgatgag acgttgatcg gcacgtaag                              39

<210> SEQ ID NO 13
<211> LENGTH: 40
<212> TYPE: DNA
<213> ORGANISM: Artificial Sequence
<220> FEATURE:
<223> OTHER INFORMATION: FT19 PCR primer

<400> SEQUENCE: 13
ggttggtttg cgcattcagc gctaaccgtt tttatcaggc                             40

<210> SEQ ID NO 14
<211> LENGTH: 25
<212> TYPE: DNA
<213> ORGANISM: Artificial Sequence
<220> FEATURE:
<223> OTHER INFORMATION: FT121 primer

<400> SEQUENCE: 14
catgcccggg tacctttcta ttctc                                            25

```
<210> SEQ ID NO 15
<211> LENGTH: 79
<212> TYPE: DNA
<213> ORGANISM: Artificial Sequence
<220> FEATURE:
<223> OTHER INFORMATION: FT126 template

<400> SEQUENCE: 15
catgtttcgg ccgagccccc accctgcgga tgagccagca aagtctagcc ggcagagtga    60
gaatagaaag gtacccggg                                                 79
```